(12) United States Patent
Ouchi

(10) Patent No.: US 7,857,749 B2
(45) Date of Patent: Dec. 28, 2010

(54) TREATMENT TOOLS FOR ENDOSCOPE

(75) Inventor: Teruo Ouchi, Saitama-ken (JP)

(73) Assignee: Hoya Corporation, Tokyo (JP)

( * ) Notice: Subject to any disclaimer, the term of this patent is extended or adjusted under 35 U.S.C. 154(b) by 1073 days.

(21) Appl. No.: 10/958,394

(22) Filed: Oct. 6, 2004

(65) Prior Publication Data

US 2005/0043721 A1 Feb. 24, 2005

Related U.S. Application Data

(63) Continuation of application No. 10/081,854, filed on Feb. 25, 2002, now Pat. No. 6,814,728.

(30) Foreign Application Priority Data

| Feb. 26, 2001 | (JP) | ............................. 2001-050545 |
| Feb. 27, 2001 | (JP) | ............................. 2001-051580 |
| Mar. 1, 2001 | (JP) | ............................. 2001-056076 |
| Mar. 1, 2001 | (JP) | ............................. 2001-056212 |
| Jun. 28, 2001 | (JP) | ............................. 2001-196466 |
| Jul. 18, 2001 | (JP) | ............................. 2001-217503 |
| Jul. 18, 2001 | (JP) | ............................. 2001-217504 |
| Jul. 18, 2001 | (JP) | ............................. 2001-218138 |

(51) Int. Cl.
*A61B 1/00* (2006.01)

(52) U.S. Cl. .................. 600/104; 600/106; 600/562; 606/1

(58) Field of Classification Search ............... 600/139, 600/141, 146, 104, 562–584; 606/1; 604/95.01, 604/65.04

See application file for complete search history.

(56) References Cited

U.S. PATENT DOCUMENTS

| 3,964,468 A | * | 6/1976 | Schulz ..................... 600/564 |
| 4,271,845 A | | 6/1981 | Chikashige et al. |
| 4,353,358 A | | 10/1982 | Emerson |
| 4,653,476 A | | 3/1987 | Bonnet |
| 4,724,836 A | | 2/1988 | Okada |
| 4,911,148 A | | 3/1990 | Sosnowski et al. |
| 4,920,980 A | * | 5/1990 | Jackowski .................. 607/123 |
| 4,960,134 A | * | 10/1990 | Webster, Jr. .................. 607/116 |

(Continued)

FOREIGN PATENT DOCUMENTS

JP  48-58691  8/1973

(Continued)

OTHER PUBLICATIONS

English language Abstract of JP 48-58691.

(Continued)

*Primary Examiner*—Matthew J Kasztejna
(74) *Attorney, Agent, or Firm*—Greenblum & Bernstein, P.L.C.

(57) ABSTRACT

A tubular treatment tool is provided for an endoscope. The tubular treatment tool includes a flexible tubular member. A groove is formed on the flexible tubular member and traverses the flexible tubular member along the diameter. An operation wire is provided in the flexible tubular member. The operation wire is movable relative to the flexible tubular member along an axis of the flexible tubular member. A distal end of the operation wire is secured to the flexible tubular member at a position on a distal end side with respect to the groove. A tissue collecting device is secured at the distal end of the flexible tubular member.

5 Claims, 33 Drawing Sheets

U.S. PATENT DOCUMENTS

| | | | |
|---|---|---|---|
| 5,058,603 A | 10/1991 | Doi et al. | |
| 5,169,386 A * | 12/1992 | Becker et al. | 606/192 |
| 5,284,128 A | 2/1994 | Hart | |
| 5,403,297 A * | 4/1995 | Imran | 604/531 |
| 5,441,483 A * | 8/1995 | Avitall | 604/95.05 |
| 5,441,503 A * | 8/1995 | Considine et al. | 606/115 |
| 5,520,222 A | 5/1996 | Chikama | |
| 5,873,842 A | 2/1999 | Brennen et al. | |
| 5,921,982 A * | 7/1999 | Lesh et al. | 606/41 |
| 6,013,024 A | 1/2000 | Mitsuda et al. | |
| 6,017,339 A * | 1/2000 | Sadamasa | 606/46 |
| 6,093,155 A * | 7/2000 | Ouchi | 600/569 |
| 6,113,556 A * | 9/2000 | Avitall | 600/585 |
| 6,248,062 B1 | 6/2001 | Adeler et al. | |
| 6,398,776 B1 * | 6/2002 | Sekino et al. | 604/524 |
| 6,814,728 B2 | 11/2004 | Ouchi | |

FOREIGN PATENT DOCUMENTS

| | | |
|---|---|---|
| JP | 52-33146 | 8/1977 |
| JP | 53-10396 | 3/1978 |
| JP | 55-109502 | 7/1980 |
| JP | 56-053401 | 5/1981 |
| JP | 57-110227 | 7/1982 |
| JP | 58-070203 | 5/1983 |
| JP | 58-81021 | 5/1983 |
| JP | 58-142019 | 9/1983 |
| JP | 61-067710 | 5/1986 |
| JP | 62-15217 | 4/1987 |
| JP | 64-4335 | 2/1989 |
| JP | 2-045030 | 2/1990 |
| JP | 2-082933 | 3/1990 |
| JP | 2-206420 | 8/1990 |
| JP | 2-118505 | 9/1990 |
| JP | 2-264649 | 10/1990 |
| JP | 2-141423 | 11/1990 |
| JP | 3-13898 | 2/1991 |
| JP | 3-126445 | 5/1991 |
| JP | 4-132531 | 5/1992 |
| JP | 4-108505 | 9/1992 |
| JP | 5-000142 | 1/1993 |
| JP | 5-142 | 1/1993 |
| JP | 5-038342 | 2/1993 |
| JP | 5-323207 | 12/1993 |
| JP | 6-1128 | 1/1994 |
| JP | 6-5769 | 2/1994 |
| JP | 6-44401 | 11/1994 |
| JP | 8-089475 | 4/1996 |
| JP | 9-135836 | 5/1997 |
| JP | 11-226020 | 8/1999 |
| JP | 2002-248173 | 9/2002 |
| JP | 2002-253492 | 9/2002 |

OTHER PUBLICATIONS

English language Abstract of JP 58-81021.
English language Abstract of JP 58-142019.

* cited by examiner

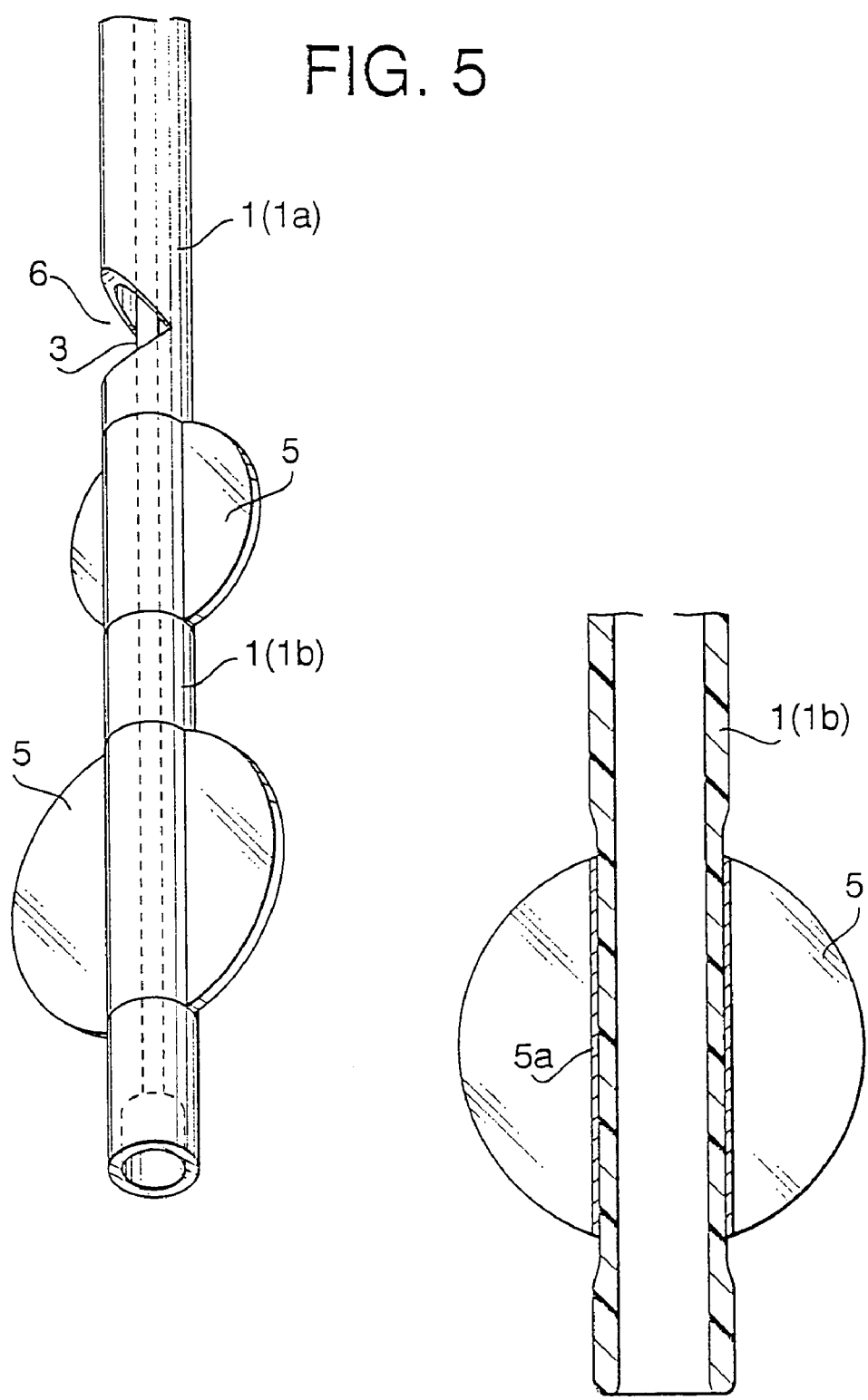

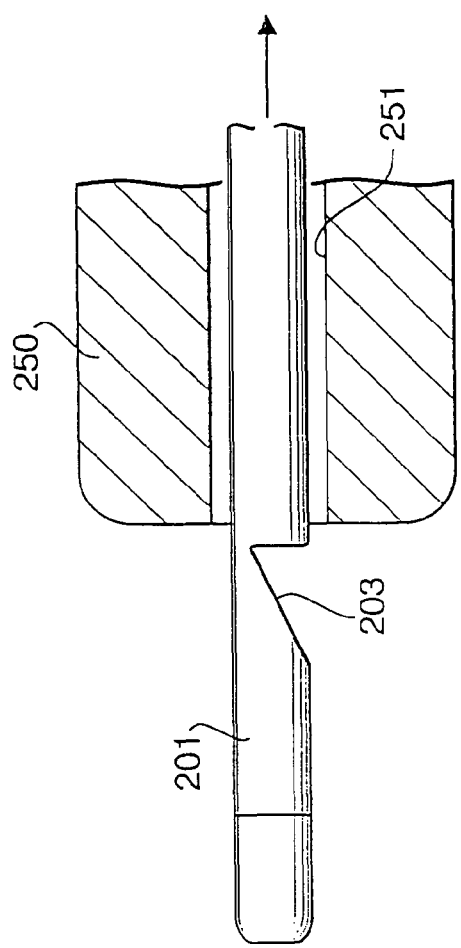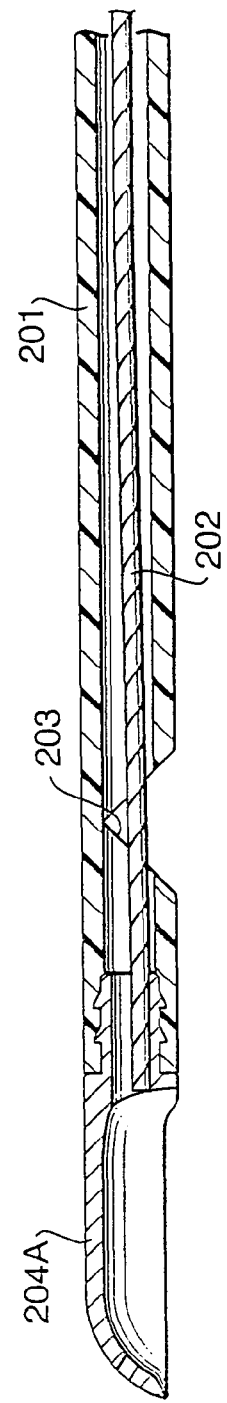

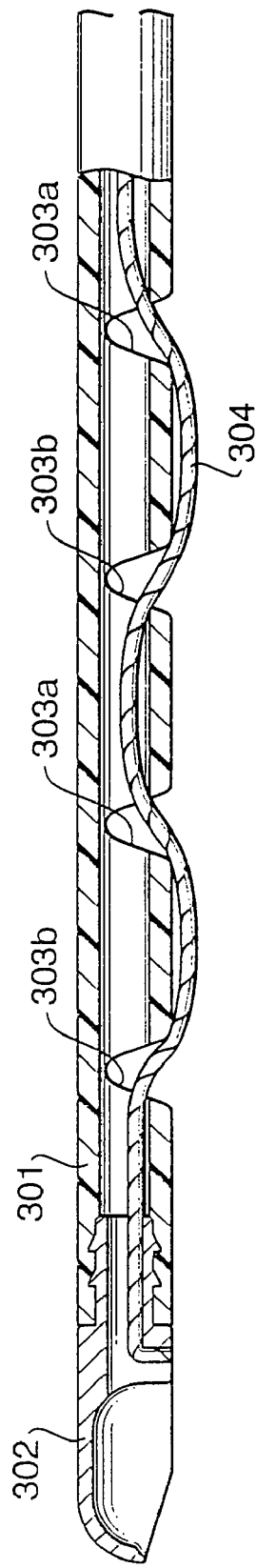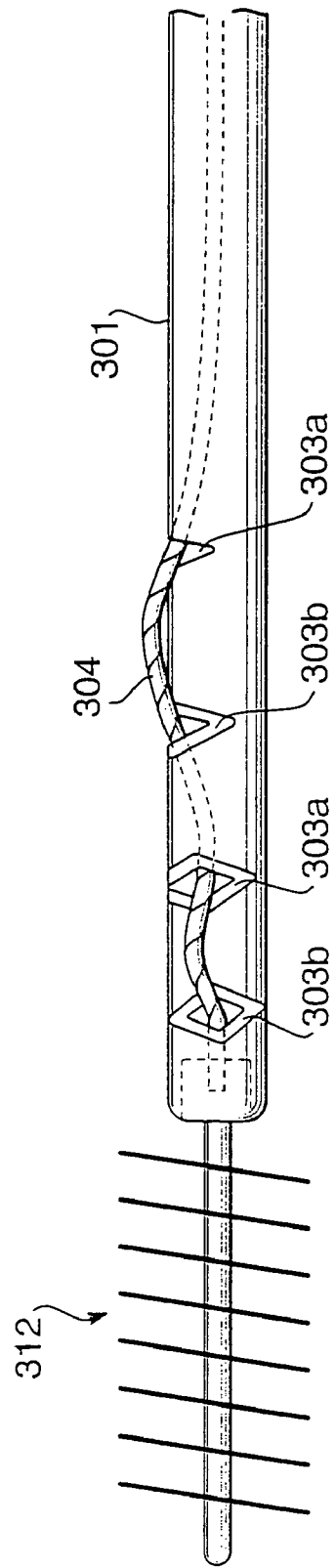
FIG.21
FIG.22

TREATMENT TOOLS FOR ENDOSCOPE

This application is a continuation of U.S. patent application Ser. No. 10/081,854, filed on Feb. 25, 2002, which is now U.S. Pat. No. 6,814,728 issued on Nov. 9, 2004, the disclosure of which is expressly incorporated herein by reference in its entirety.

BACKGROUND OF THE INVENTION

The present invention relates to a measurement tool or treatment tool for an endoscope.

A measurement tool for an endoscope is typically used for measuring a size of an ulcer or the like on a mucous membrane in a human cavity. The measurement tool is generally configured such that graduations are formed at a tip end portion of a flexible shaft, which is detachably inserted through an instrument tool insertion channel of the endoscope. An example of such a measurement tool is disclosed in Japanese Utility Model Publication HEI 6-44401.

With the measurement tool configured as described above, a size only in one direction can be measured, and a length in another direction cannot be measured. In order to measure the size of an object in two different direction, a direction where the graduations are provided should be changed. However, at the tip of the endoscope, at which a positional relationship with respect to the ulcer is limited, it is difficult to change the orientation of the distal end of the endoscope. Thus, it is almost impossible to directly measure the length of the object (e.g., ulcer) in two different directions. Therefore, a length in one direction should be guessed based on the measured length.

The Japanese Utility Model Publication HEI 6-44401 teaches a measurement tool provided with a flexible tube having two slits, which traverse the flexible tube in the diameter direction, at a certain interval along the axis of the flexible tube. By operation an operation wire, the distal end portion of the flexible tube, on which gradations are formed, is bent to form a T-shape. However, in such a configuration, the flexible tube is bent by 180 degrees at one of the two slits. Therefore, when such a bending operation is repeated, the flexible tube may be broken, at the slit, within a relatively short period of time.

Another typical tool for an endoscope is an injection tube for injecting contrast medium. A conventional injection tube is typically formed as a single tube made of flexible resin such as tetrafluoroethylene. An injection mouth is provided at the proximal end of the injection tube. At the distal end thereof, an end tip may be secured. In some injection tubes, a core metal is inserted so that the tube is not folded.

The tubular tool as described above is inserted in a treatment tool channel of an endoscope. In the conventional treatment tool, an orientation or a direction of a distal end portion of the tubular tool, which is protruded from the distal end of the endoscope, cannot be controlled. Therefore, according to the conventional art, the distal end portion of the flexible tube is formed to have tendency to bend in a predetermined direction. Even with such a tubular tool, it is still difficult to insert the tubular tool in a diverging tube at a deep portion of a bile duct or bronchial tubes.

Another typical treatment tool for an endoscope is a bendable treatment tool used for collecting tissues from a mucous membrane inside a human cavity.

As such treatment tools for collecting human tissues, ones having a brush tool or spoon tool are secured onto a tip end of a flexibly bendable sheath. An example of such a tool is described in Japanese Patent Provisional Publication HEI 05-142.

Conventional tools for collecting human tissues, as described in the above-described publication, are configured as precision instrument such that link members rotatable at respective rotation axes, which are perpendicular to the axis of the flexible tube, are provided at the tip end portion of the flexible sheath. The link members are configured to be bent/expanded upon back/forth movement of an operation wire.

With this precise structure, it is difficult to clean the tool completely after operation thereof. Further, due to the precise structure, the tool easily malfunctions. Due to the precise structure, such tools are relatively expensive and may not be disposable. Accordingly, the conventional tools may be reused in unstable condition.

Another typical treatment tool for an endoscope is a catheter, which is inserted in the forceps channel of an endoscope, and is used for feeding of chemicals or suction of bodily fluids.

The catheter for an endoscope is generally formed of a flexible tube having a simple structure. In order to lead the distal end of the catheter to a target position, it is preferable that the direction of the distal end portion is remotely changeable.

FIG. 35 shows a structure of a conventional catheter for an endoscope. As shown in FIG. 35, the conventional catheter includes a flexible tube 501. Inside the flexible tube 501, an operation wire 502 is loosely inserted. At the distal end portion of the flexible tube 1, a pair of holes 503 are formed, which are spaced along the axial direction by a predetermined amount. Between the holes 503, the operation wire 502 is located outside the flexible tube 501 and extends along the axis of the flexible tube 501. Further, the flexible tube 1 is provided with a plurality of circumferential grooves 504 at a predetermined interval so that the flexible tube 1 is easily bent.

In the catheter configured as described above, if the operation wire 502 has tendency to bend in a certain direction, the flexible tube 1 may meander. In such a case, the catheter cannot be used. Therefore, generally twisted wires having less rigidity are used as the operation wire 502.

When the operation wire 2 is pulled, the distal end portion of the flexible tube 501 is bent as indicated by two-dotted lines in FIG. 35. However, even if the operation wire is pushed, due to its low rigidity, the distal end portion of the flexible tube 1 may not bend. Thus, according to the conventional structure, it is very difficult to lead the distal end of the catheter to a desired direction.

A cytodiagnosis brush is known as treatment tool for an endoscope. Generally, the cytodiagnosis brush is configured such that a brush shaft provided with radially planted brush at the distal end portion thereof is connected with the distal end of a closely wounded coil pipe, which can be inserted in the treatment tool insertion channel of the endoscope.

Endoscopes should be cleaned and disinfected completely after they are used. However, for the cytodiagnosis brush described above, it is difficult to completely clean and disinfect inside the coil pipe. Therefore, in order to avoid contagion between patients via the cytodiagnosis brush, it must be disposed when it is used once, which has been considered wasteful.

Another typical treatment tool for an endoscope is a biopsy forceps for collecting biopsy tissues from the human cavity.

The biopsy forceps is generally configured such that an operation wire is movably inserted in a flexible sheath, and by moving the operation wire, a pair of forceps cups provided at the distal end of the flexible sheath are opened/closed.

In a conventional biopsy forceps configured as above, the direction of the distal end portion of the sheath cannot be changed. FIG. 46 schematically shows a branched portion of a brachial tube, in which an endoscope 750 is inserted. In FIG. 46, 701 denotes a flexible sheath and 702 denotes forceps cups. In this example, the endoscope should be inserted to a branched tube having a tumor 100. However, since the direction of the distal end portion of the flexible sheath 701 cannot be changed, when the flexible sheath 701 is protruded from the distal end of the endoscope, the flexible sheath enters the other tube as shown in FIG. 47.

Even if the flexible sheath 701 can be introduced in the desired tube, as shown in FIG. 48, the tissues are collected with the forceps cups 702 abutting against the tumor 100 from the side. Therefore, invasion area of malignant lesion may not be diagnosed accurately.

In Japanese Utility Model Publication SHO 52-33146 or Japanese Patent Publication SHO 53-10396, a biopsy forceps having a mechanism to bend the flexible sheath at the distal end portion thereof is described. However, if the sheath is very thin, such a mechanism cannot be practically employed in view of the strength and operability.

A further typical treatment tool for an endoscope is a high-frequency cutting tool used for cutting human tissues using a high-frequency.

FIG. 52 shows a structure of a conventional high-frequency cutting tool for an endoscope. As shown in FIG. 52, the conventional high-frequency cutting tool includes a flexible tube 801 made of electrically insulating material. Inside the flexible tube 801, a conductive wire 802 is loosely inserted. At the distal end portion of the flexible tube 801, a pair of holes 803 are formed, which are spaced along the axial direction by a predetermined amount. Between the holes 803, the conductive wire 802 is located outside the flexible tube 801 and extends along the axis of the flexible tube 801. Further, the flexible tube 801 is provided with a plurality of circumferential grooves 804 at a predetermined interval so that the flexible tube 1 is easily bent. Such a structure is disclosed in Japanese Patent Publication SHO 64-4335.

By pulling the conductive wire as indicated by arrow in FIG. 52, the distal end portion of the flexible tube 1 between the pair of holes 803 is bent as indicated by two-dotted lines in FIG. 52.

FIG. 51 shows a usage of the high-frequency cutting tool described above. The distal end portion of the flexible tube 1 is inserted in an opening of bile duct 102 communicating with the duodenum 101, and the high-frequency current is applied to the conductive wire 802. Then, the tissues at the opening are cut. In FIG. 51, 850 denotes the endoscope and 851 denotes the treatment tool channel of the endoscope 850.

In the conventional high-frequency cutting tool as described above, the bending amount of the distal end portion of the flexible tube 801 is determined only by the pulling force of the conductive wire 802, and in accordance with the bending amount, the cutting depth 800A of the tissues is determined.

However, the bending amount cannot be controlled accurately, and therefore, the cutting depth 800A may not be different from the intended amount.

SUMMARY OF THE INVENTION

According to some embodiments of the invention, there is provided a measurement tool for an endoscope, with which a two-dimensional size of an object such as an ulcer can be measured relatively easily and accurately.

According to some embodiments of the invention, there is provided a tubular treatment tool for an endoscope, which is configured such that the orientation of the distal end portion thereof can be changed arbitrarily with operation of an operation unit, and can be inserted in the diverging tube located deep inside the bile duct or bronchial tubes.

According to some embodiments of the invention, there is provided a bendable treatment tool for an endoscope, which has a relatively simple structure. Because of the simple structure, the tool may be cleaned easily, and is hard to malfunction. Further, due to its simple structure, the tool may be manufactured at a relatively low cost, and thus can be provided as a disposable tool.

According to some embodiments of the invention, there is provided a measurement tool for an endoscope, which has a relatively high durability, and can be manufactured at a relatively low manufacturing cost.

According to one embodiment of the invention, there is provided a catheter for an endoscope operable with an operation wire. The distal end portion of the catheter may be bent not only by pulling the operation wire but also pushing the operation wire so that the distal end portion of the flexible tube can be directed in a desired direction.

According to some embodiments of the invention, there is provided a cytodiagnosis brush which can be cleaned and disinfected completely after usage, and can be used repeatedly without contagion among patients.

According to some embodiments of the invention, there is provided a biopsy forceps, a direction of the distal end portion of which can be changed without employing a complicated mechanism and/or operation.

According to one embodiment of the invention, there is provided a high-frequency cutting tool with which the bending amount of the distal end portion of the flexible tube is controlled accurately so that the cutting amount can be adjusted to the desired amount.

In view of the above, according to the invention, there is provided a measurement tool for an endoscope, which is provided with a flexible shaft to be inserted in a treatment tool insertion channel of the endoscope, and an elastic sheet member secured to a distal end portion of the flexible shaft.

Optionally, the distal end portion of the flexible shaft may be bendable at a position on the proximal end side with respect to the elastic sheet member, the distal end portion of the flexible shaft being bendable in response to an operation at a proximal end of the flexible shaft.

Further optionally, the sheet member may include a substantially circular sheet.

In this case, the sheet member may include a plurality of sheets having different diameters, the plurality of sheets being secured to the flexible shaft at different positions.

The graduations may be formed on the sheet member.

In a particular case, the sheet member may be detachably secured to the flexible shaft.

The measurement tool may further include an elastic annular sheet secured to the flexible shaft, the annular sheet surrounding the sheet member.

According to another aspect, there is provided a tubular treatment tool for an endoscope, which includes a flexible tubular member, a groove traversing the flexible tubular member in a direction of a diameter thereof being formed, and an operation wire inserted in the flexible tubular member, the operation wire being movable relative to the flexible tube along an axis of the flexible tube, a distal end of the operation wire being secured to the flexible tube at a position on a distal end side with respect to the groove.

Optionally, the groove may have a V-shaped cross section.

Further, a tissue collecting device may be secured at the distal end of the flexible tube.

According to a further aspect of the invention, there is provided a tubular treatment tool for an endoscope, which includes a flexible tubular member, at least one pair of grooves each traversing the flexible tubular member in a direction of a diameter thereof being formed, and an operation wire inserted in the flexible tubular member, the operation wire being movable relative to the flexible tube along an axis of the flexible tube, the operation wire running outside of the tubular member through one of the pair of grooves and running inside of the tubular member so that the operation wire is located outside of the flexible tubular member between the pair of grooves, a distal end of the operation wire being secured to the flexible tube at a position on a distal end side with respect to the pair of grooves.

Optionally, each of the grooves may have a V-shape cross section.

Further optionally, at least one pair of grooves may include a plurality of pairs of grooves, the operation wire being located outside of the flexible tubular member between two grooves of each pair of the plurality of pair of grooves.

In this case, the plurality of pairs of grooves may be located at different positions along the circumference of the flexible tubular member.

Still optionally, a tissue collecting device may be secured at the distal end of the flexible tube.

According to another aspect of the invention, there is provided a measurement tool for an endoscope, which is provided with a flexible tubular member, a groove traversing the flexible tubular member in a direction of a diameter thereof being formed, at least a distal end side, with respect to the groove, of the flexible tubular member being formed with graduations, and an operation wire inserted in the flexible tubular member, the operation wire being movable relative to the flexible tube along an axis of the flexible tube, a distal end of the operation wire being secured to the flexible tubular member at a position on a distal end side with respect to the groove.

Optionally, the groove may have a V-shaped cross section.

Still optionally, a fluid injection mouth, which communicates with the flexible tubular member, may be provided at a proximal end portion of the flexible tubular member.

According to a further aspect of the invention, there is provided a catheter for an endoscope, which is provided with a flexible tubular member through which fluid passes, a groove traversing the flexible tubular member in a direction of a diameter thereof being formed, the groove having a V-shaped cross section, and an operation wire inserted in the flexible tubular member, the operation wire being movable relative to the flexible tube along an axis of the flexible tube, a distal end of the operation wire being secured to the flexible tubular member at a position on a distal end side with respect to the groove, a pair of holes being formed on both sides, along an axis of the flexible tubular member, of the groove, the operation wire being inserted through the pair of holes so that the operation wire being located outside of the flexible tubular member at a position between the pair of holes.

According to a further aspect of the invention, there is provided a cytodiagnosis brush for an endoscope, which is provided with a flexible tubular member, a brush shaft, a brush being radially planted at a distal end portion of the brush shaft, and a stopper secured to the proximal end of the brush shaft, the stopper being fixed to the flexible tubular member at a distal end portion thereof, a fluid passage along an axis of the flexible tubular member being defined in the stopper.

Optionally, a groove traversing the flexible tubular member in a direction of a diameter thereof may be formed, the groove having a V-shaped cross section, and the cytodiagnosis brush further comprises an operation wire inserted in the flexible tubular member, the operation wire being movable relative to the flexible tube along an axis of the flexible tube, a distal end of the operation wire being secured to the flexible tubular member at a position on a distal end side with respect to the groove, a pair of holes being formed on both sides, along an axis of the flexible tubular member, of the groove, the operation wire being inserted through the pair of holes so that the operation wire is located outside of the flexible tubular member at a position between the pair of holes.

According to another aspect of the invention, there is provided a biopsy forceps for an endoscope, which is provided with a flexible tubular member, an operation wire inserted through the flexible tubular member, a pair of forceps cups secured to the distal end of the flexible tubular member, a link mechanism with which the pair of forceps cups open and close upon operation of the operation wire, an incision being formed, from an outer surface of the flexible tubular member, at a distal end portion of the flexible tubular member along a direction of a diameter of the flexible tubular member.

Optionally, an end of the incision may be located substantially at a position past the inner diameter of the flexible tubular member.

In a particular case, the incision is a slit. Alternatively, the incision may be a groove having a V-shaped cross section.

According to a further aspect of the invention, there is provided a high-frequency cutting tool for an endoscope, which is provided with an electrically insulating flexible tubular member, at least one pair of grooves each traversing the flexible tubular member in a direction of a diameter thereof being formed, and a conductive wire inserted in the flexible tubular member, the conductive wire being movable relative to the flexible tube along an axis of the flexible tube, wherein a groove traversing the flexible tubular member in a direction of a diameter thereof is formed, the groove having a V-shaped cross section, a distal end of the conductive wire being secured to the flexible tubular member at a position on a distal end side with respect to the groove, a pair of holes being formed on both sides, along an axis of the flexible tubular member, of the groove, the conductive wire being inserted through the pair of holes so that the operation wire is located outside of the flexible tubular member at a position between the pair of holes.

BRIEF DESCRIPTION OF THE ACCOMPANYING DRAWINGS

FIG. 5 is a side view of a distal end portion of a measurement tool for an endoscope according to a second embodiment of the invention;

FIG. 6 is a cross-sectional side view of a distal end portion of the measurement tool according to the second embodiment;

FIG. 15 shows a groove of a tubular treatment tool according to a fourth embodiment of the invention;

FIG. 16 shows a tubular treatment tool according to a fifth embodiment of the invention, a spoon being secured to the tip thereof;

FIG. 21 is a cross-sectional side view of a distal end portion of a bendable treatment tool according to a second embodiment of the invention;

FIG. 22 is a side view of a distal end portion of a bendable treatment tool according to a third embodiment of the invention;

Figure 43:
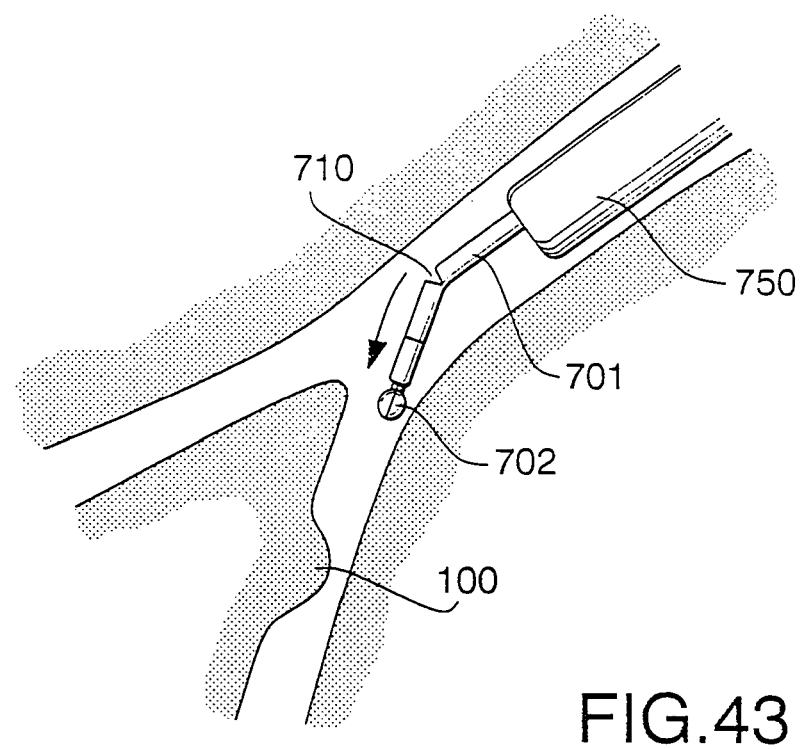
Figure 44:
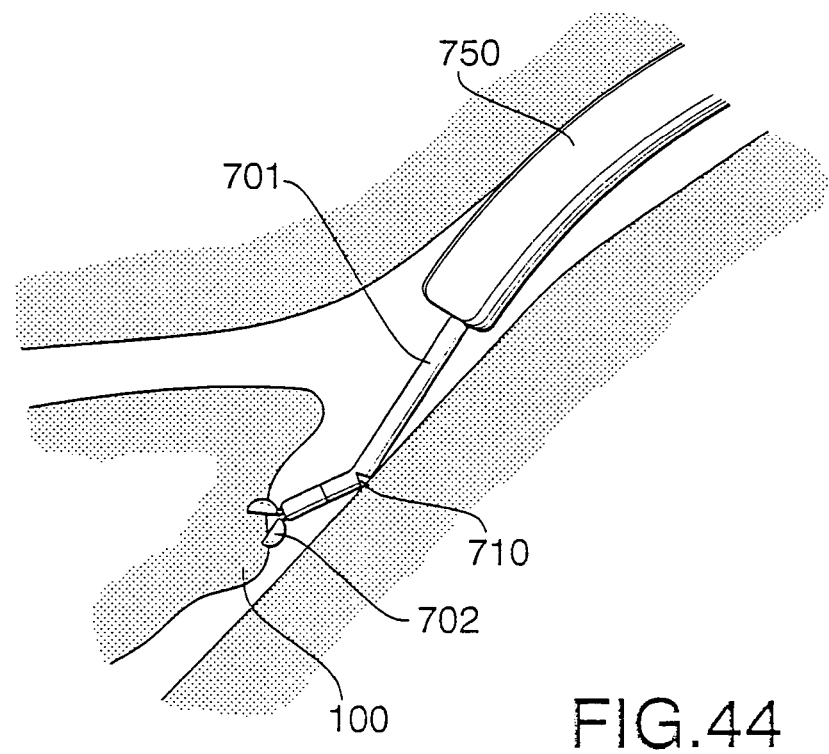
Figure 45:
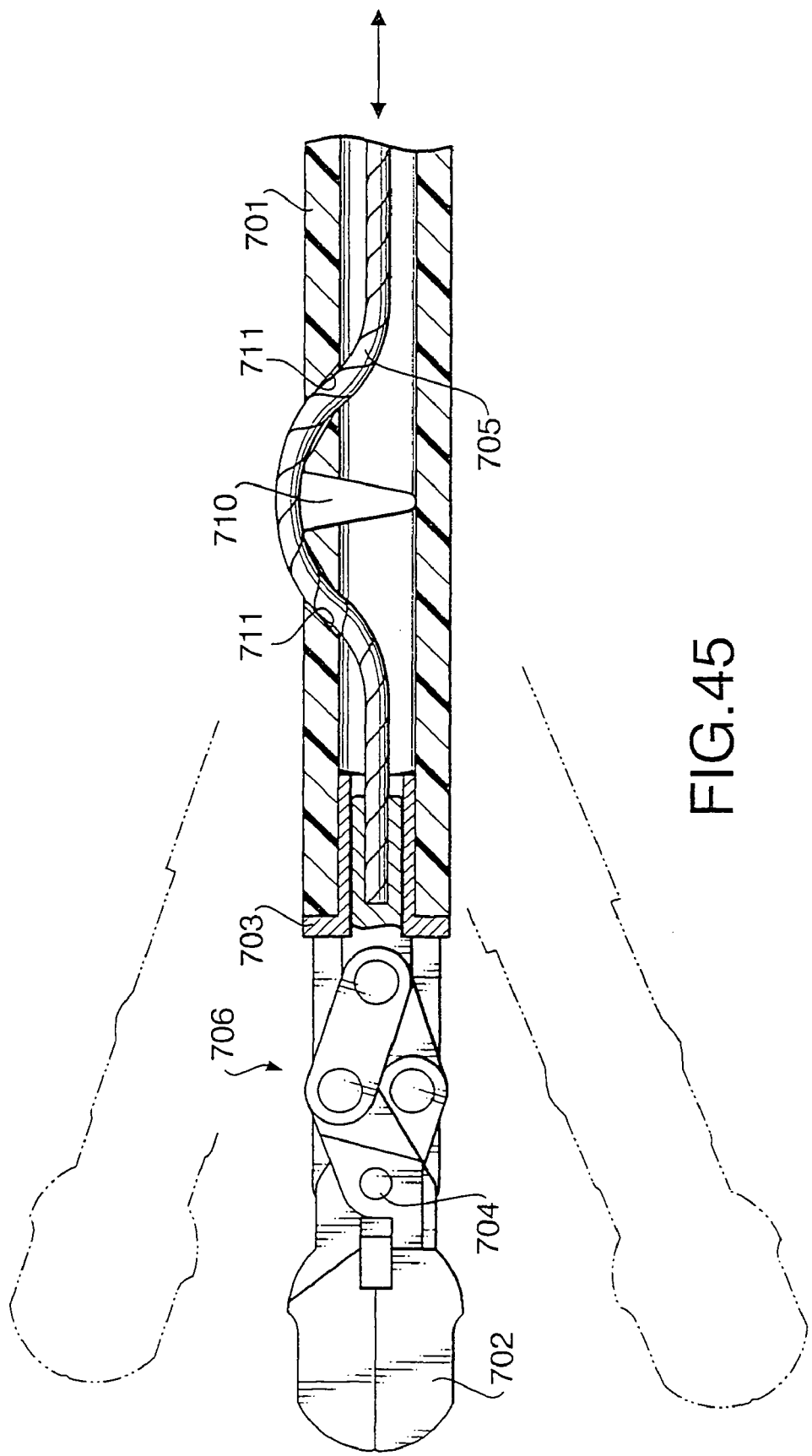
Figure 46:
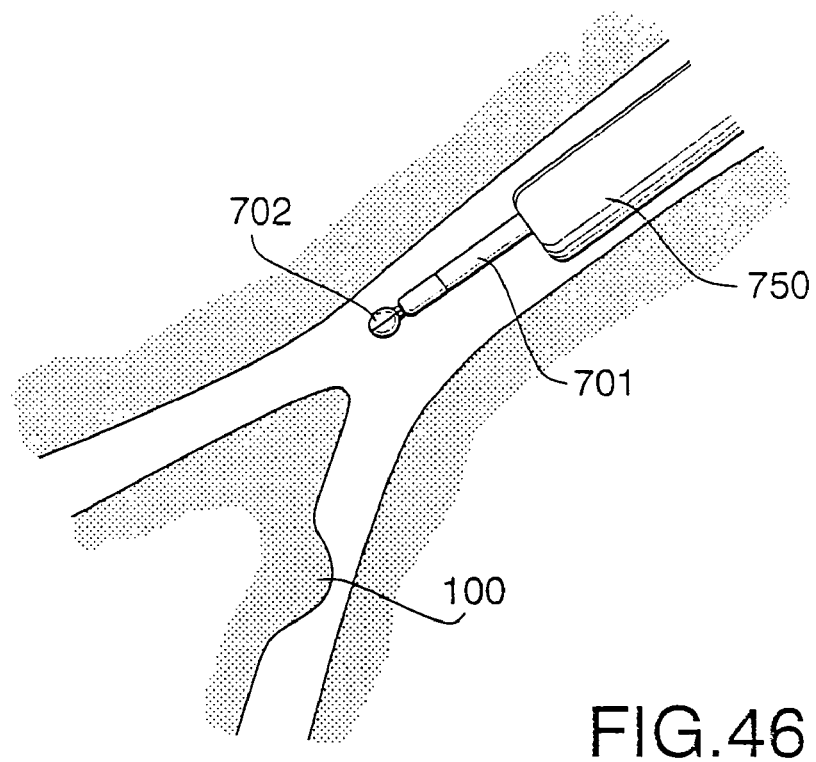
Figure 47:
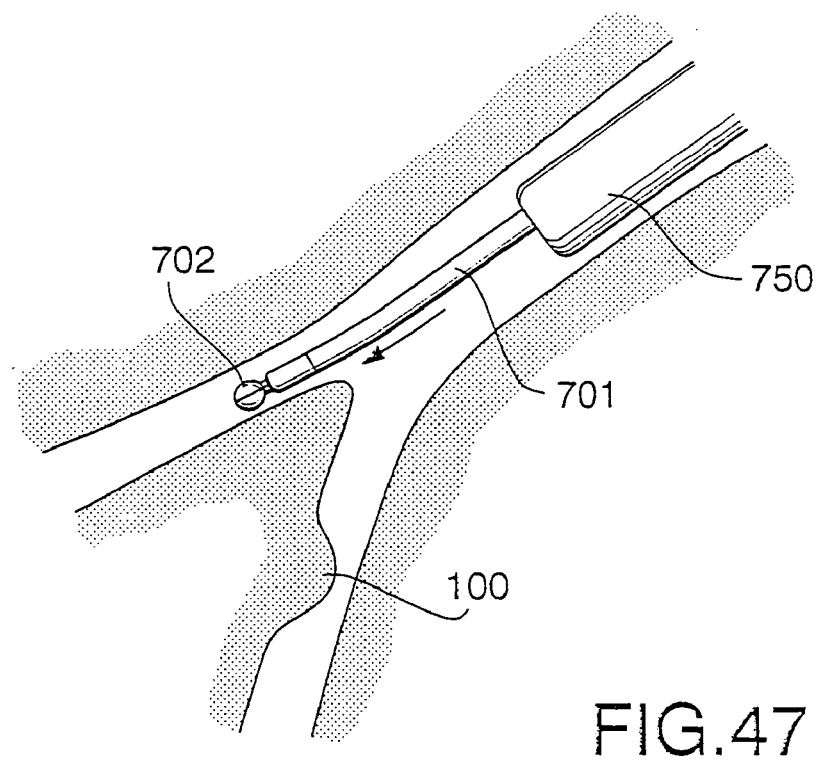
Figure 48:
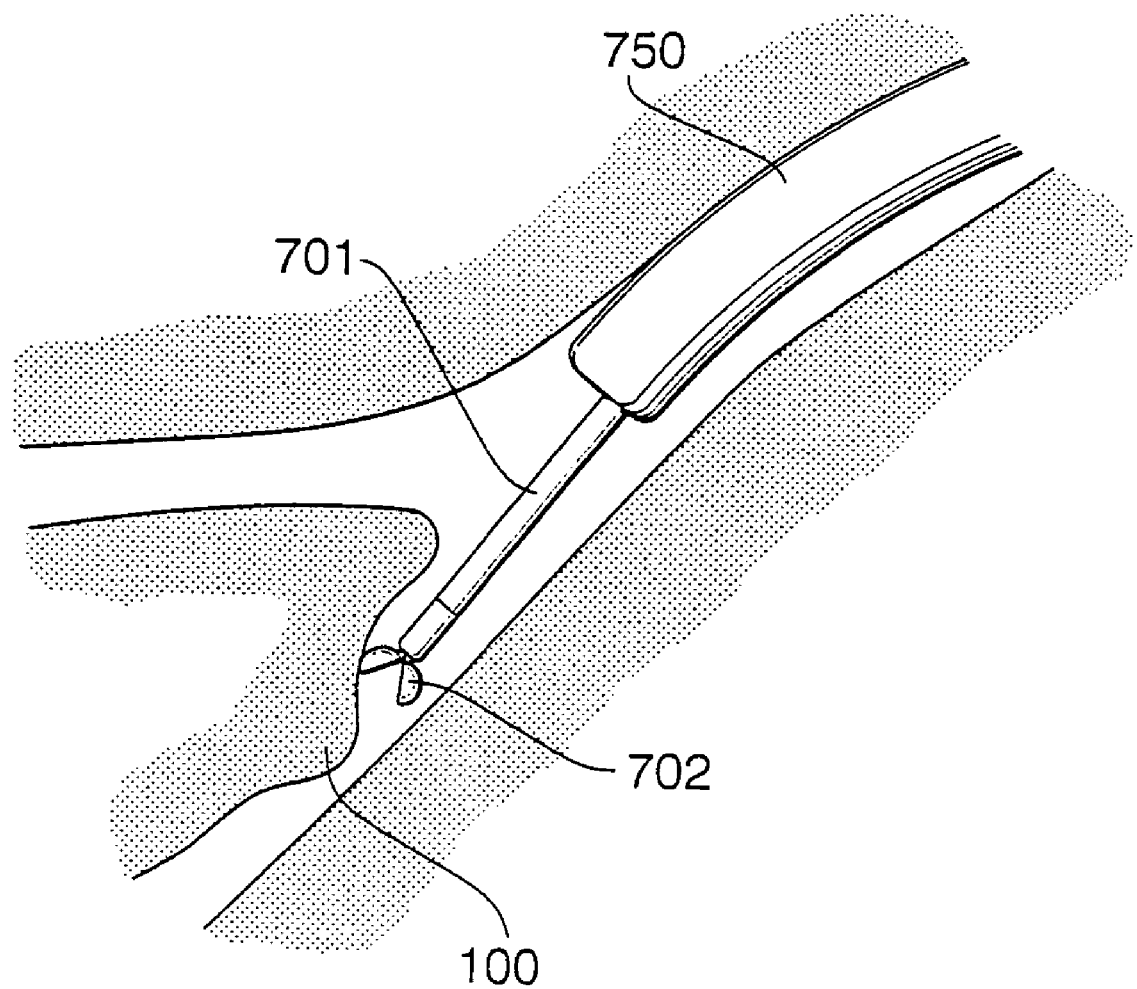
Figure 49:
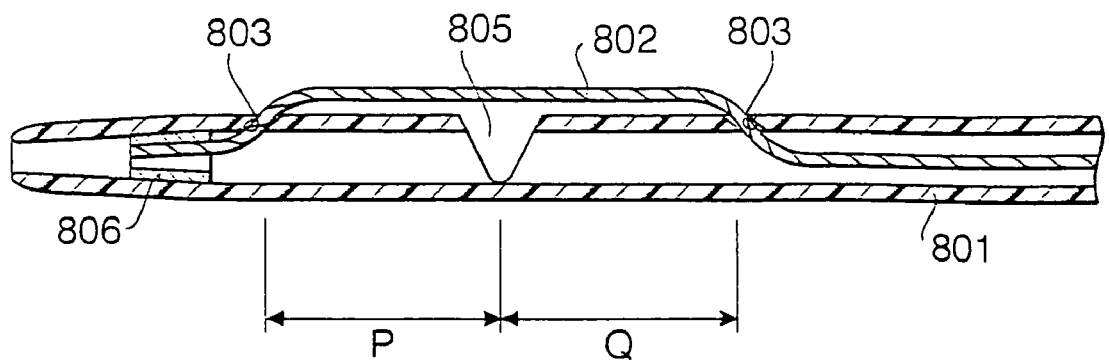
Figure 50:
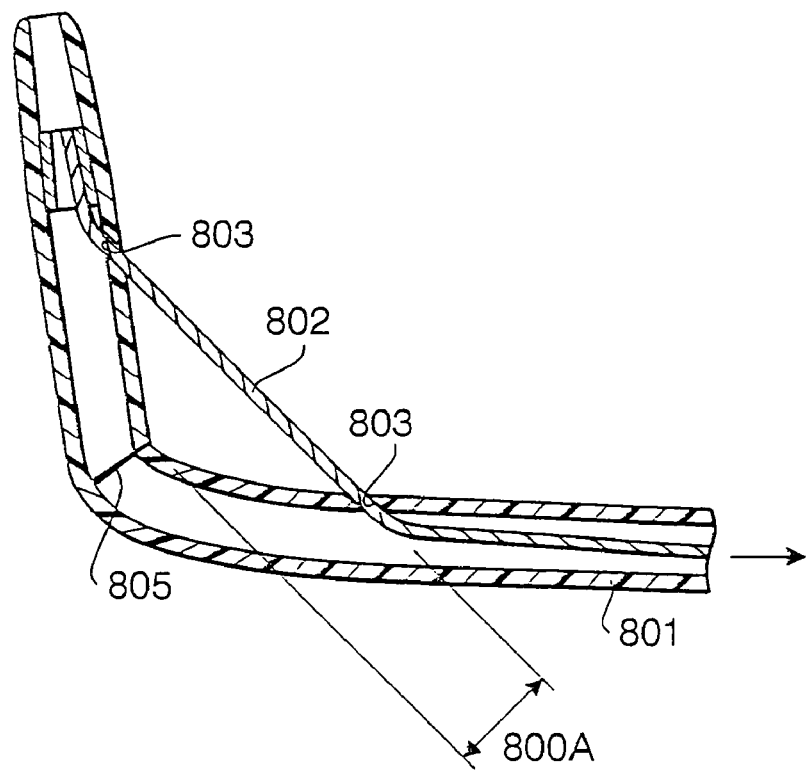
Figure 51:
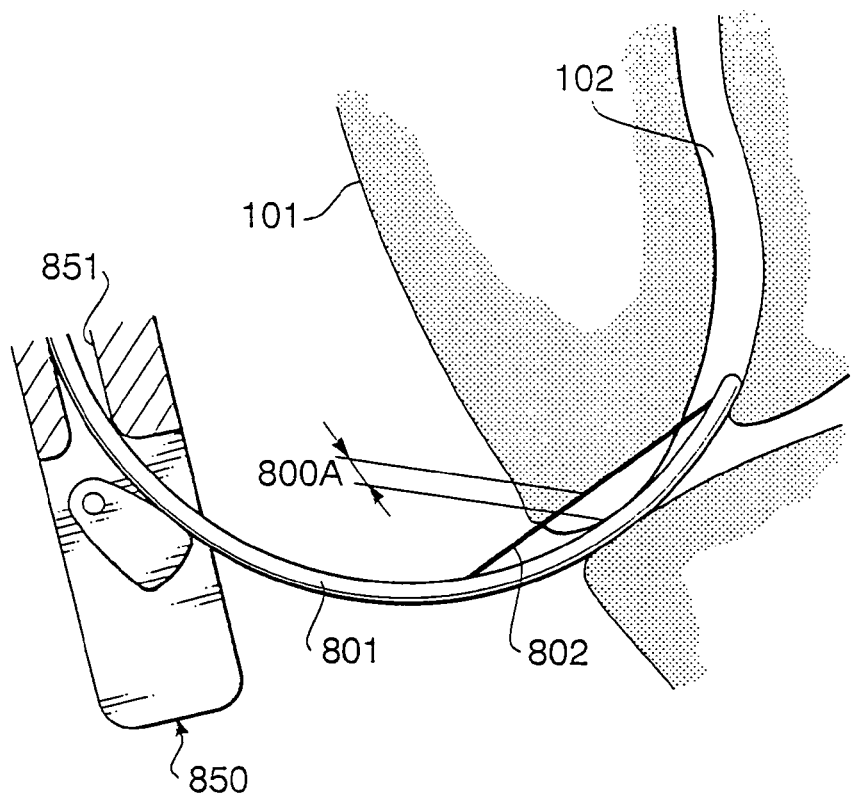
Figure 52:
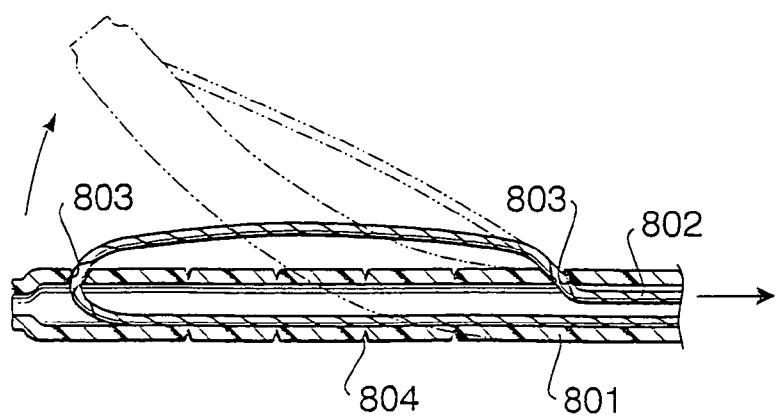

FIG. 43 schematically shows the biopsy forceps according to the first embodiment when in use;

FIG. 44 schematically shows the biopsy forceps according to the first embodiment when in use;

FIG. 45 is a cross-sectional side view showing a distal end portion of a biopsy forceps according to a second embodiment;

FIG. 46 schematically shows the conventional biopsy forceps when in use;

FIG. 47 schematically shows the conventional biopsy forceps when in use;

FIG. 48 schematically shows the conventional biopsy forceps when in use;

FIG. 49 is a cross-sectional side view of a distal end portion of a high-frequency cutting tool according to an embodiment of the invention;

FIG. 50 is a cross-sectional side view of the distal end portion of the high-frequency cutting tool according to the embodiment of the invention, when it is bent;

FIG. 51 schematically shows the high-frequency cutting tool when in use; and FIG. 52 is a cross-sectional side view of a distal end portion of a conventional high-frequency cutting tool.

DETAILED DESCRIPTION OF THE EMBODIMENTS

Hereinafter, embodiments according to the present invention will be described with reference to the accompanying drawings.

FIRST-FOURTH EMBODIMENTS

Figure 1:
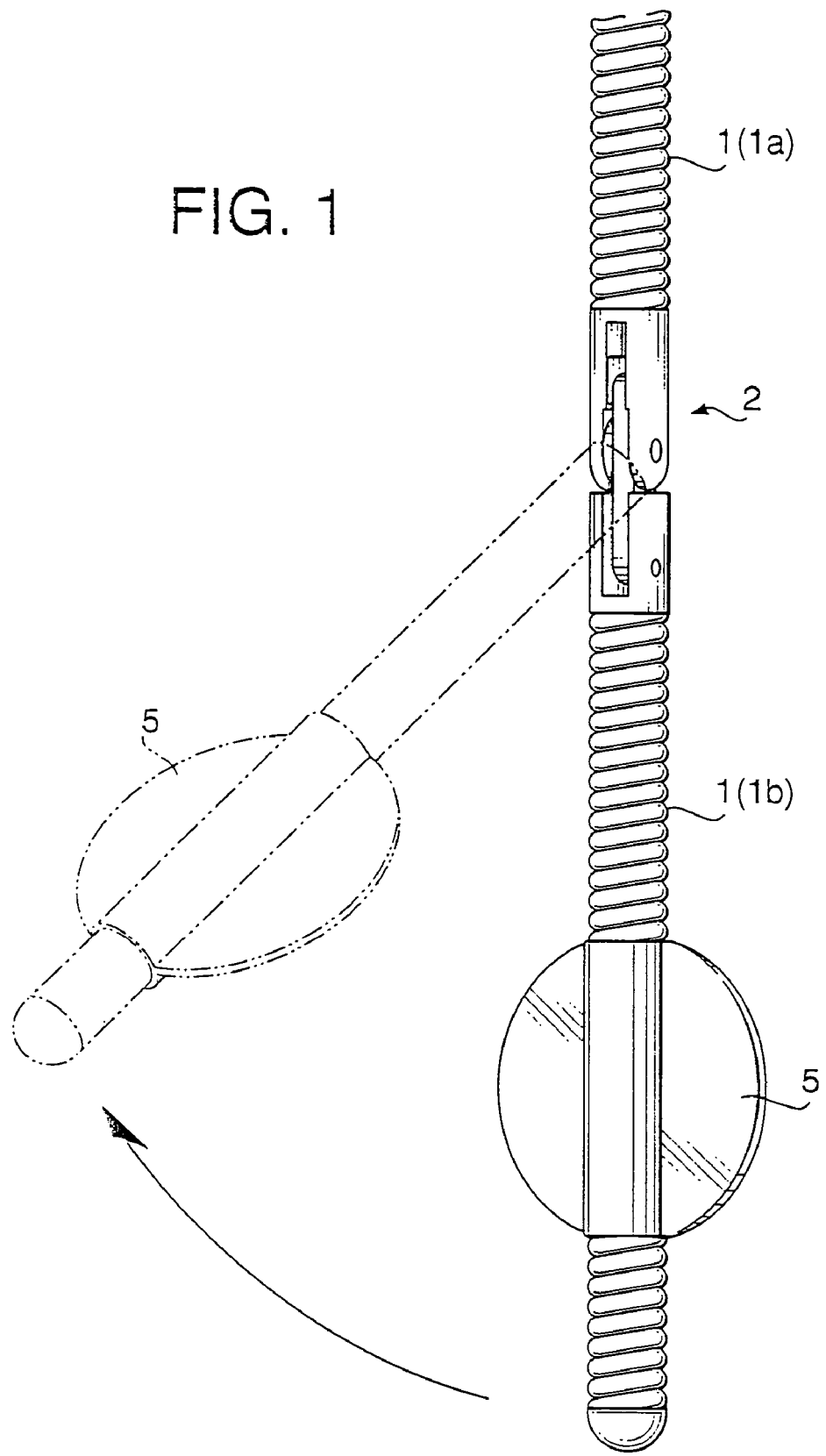
FIG. 1 is a side view of a distal end portion of a measurement tool for an endoscope according to a first embodiment of the invention.
Figure 2:
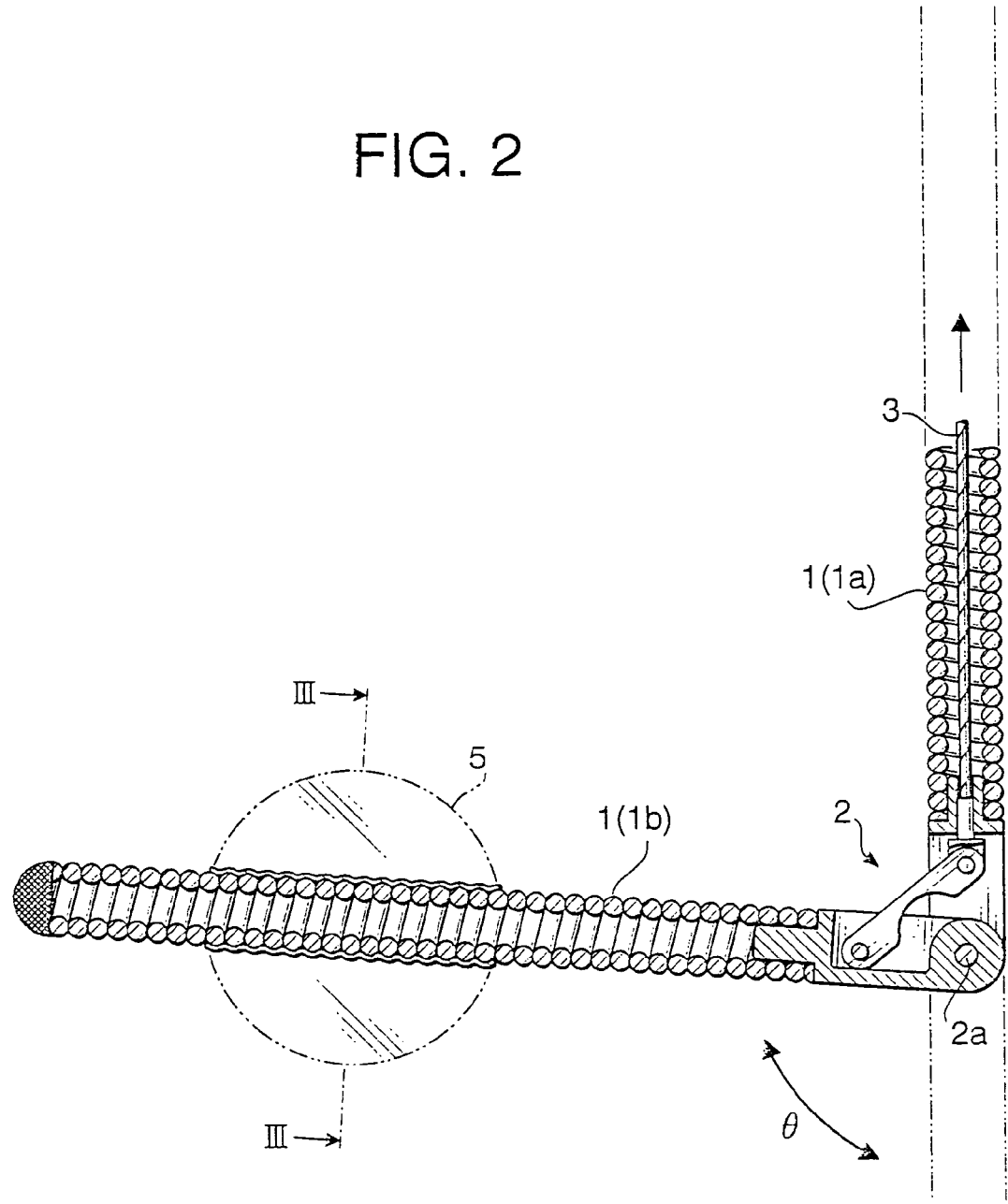
FIG. 2 is a cross-sectional side view of a distal end portion of the measurement tool according to the first embodiment.
Figure 3:
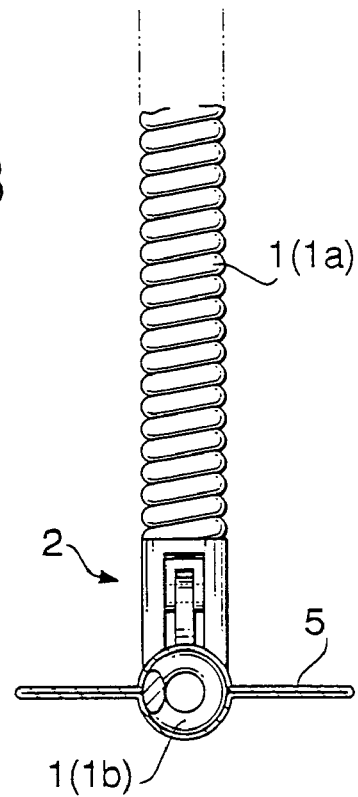
FIG. 3 is a cross-sectional view taken along line III-III of FIG. 2.
Figure 4:
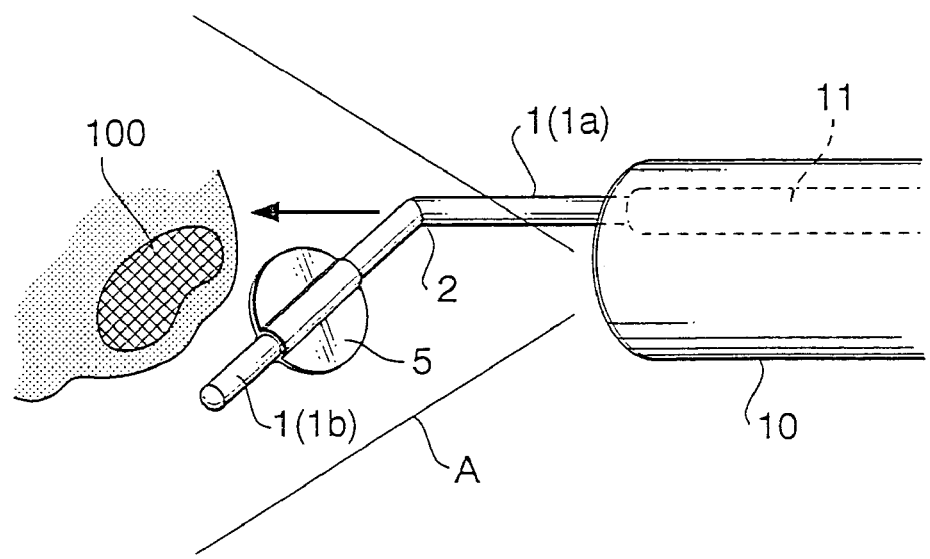
FIG. 4 shows the measurement tool in use according to the first embodiment.

FIG. 1 is a side view of a distal end portion of a flexible shaft 1 which is to be inserted in an endoscopic instrument insertion channel of an endoscope. FIG. 2 is a cross-sectional side view of the flexible tube 1, and FIG. 3 is a cross-sectional view taken along line III-III of FIG. 2. For example, an outer diameter of the flexible shaft 1 is approximately 2 mm, which is formed by a coil pipe made of a stainless steel wire. Specifically, the flexible shaft 1 includes a flexible body 1a whose length is one to two meters, and a bendable portion 1b which is a proximal end portion. The flexible body 1a and the bendable portion 1b are connected via a link mechanism 2.

Through the flexible body 1a, an operation wire 3 is inserted along the axis of the flexible body 1a. An operation unit of the endoscope is connected with the proximal end of the flexible body 1a of the flexible tube 1. The operation wire 3 is movable in forward/backward direction in response to an operation of the operation unit.

By operating the operation wire 3 to move toward the proximal end (which will be referred to as a backward movement), the bendable portion 1b rotates about a shaft 2a of the link mechanism 2, and the flexible tube 1 is bent at the link mechanism 2 as best seen in FIG. 2. The maximum bendable angle θ is preferably within a range of 30° to 120°. More preferably, the maximum bendable angle θ may be approximately 90°.

At an intermediate portion, along the axis of the bendable portion 1b, a circular sheet 5, whose diameter is 2-10 mm is secured. The sheet 5 is made of elastic material such as a silicon rubber sheet which reforms its shape to a sheet like one after certain period of time even if it is bent.

It should be noted that the sheet 5 need not be limited to one formed of silicon rubber. One formed of synthetic resin such as polyethylene, polyamide or the like can by used. If sufficient elasticity is achieved, a kind of paper may also be used.

It is preferable that the sheet 5 has a color different from the color of the surface of the mucous membrane. Preferably, the color is non-red (including white). It may be convenient to use a half-transparent material, since the object can be observed through the half-transparent sheet.

As shown in FIG. 3, the sheet 5 is adhered onto the bendable portion 5 such that the central portion of the sheet 5 surrounds the outer circumferential surface of the bendable portion 1b. A plane in which the bendable portion 1b bends is substantially perpendicular to the surface of the sheet 5.

The measurement tool thus configured is inserted in the tool channel with the bendable portion 1b straightened with respect to the flexible body 1a as shown by solid line in FIG. 1. It should be noted that, when the measurement tool is inserted in the treatment tool channel, the sheet 5 is bent or folded so that the sheet 5 can pass through the insertion channel.

When the bendable portion 1b is protruded from the distal end of the insertion channel, the sheet 5 restores its original shape due to its elasticity. Further, the bendable portion 1b can be bent by operating the operation wire 3 at the operation unit as shown in FIG. 2. Thus, the sheet 5 can be located in front of an observation field A.

By moving the flexible shaft 1 toward the ulcer 100 so that the sheet 5 is located closely adjacent to the ulcer 100, the two-dimensional size of the ulcer 100 can be measured using the gradations on the sheet 5.

FIG. 5 shows the tip portion of a measurement tool according to the second embodiment. In the second embodiment, the flexible tube 1 is formed of tetrafluoroethylene resin. Instead of the link mechanism 2 employed in the first embodiment, a V-shaped groove 6 is formed in a direction of the diameter of the flexible tube 1. The tip end of the operation wire 3 is fixed to the bendable portion 1b. Therefore, if the operation wire 3 is pulled (i.e., moved backward), the flexible tube 1 bends at the V-shaped groove 6.

Further, a plurality of sheets 5 having different diameters are secured to the bendable portion 1b at different axial positions. With this configuration, a suitable one of the sheets 5 can be used in accordance with the size of the ulcer 100.

It should be noted that, although the sheet having a larger diameter is provided on the distal end side of the bendable portion 1b in FIG. 5, ones having smaller diameters may be arranged on the distal end side.

Furthermore, in the second embodiment, as shown in FIG. 6, the sheet 5 is formed with a cylindrical through opening 5a and elastically fitted on a smaller-diameter portion of the bendable portion 1b. With this configuration, each sheet 5 can be rotated about the axis of the bendable portion 1b.

Therefore, even though the flexible shaft 1 should be inserted obliquely toward the ulcer 100, the sheet 5 can be oriented in parallel with the surface of the mucous membrane, which enables accurate measurement.

Figure 7:
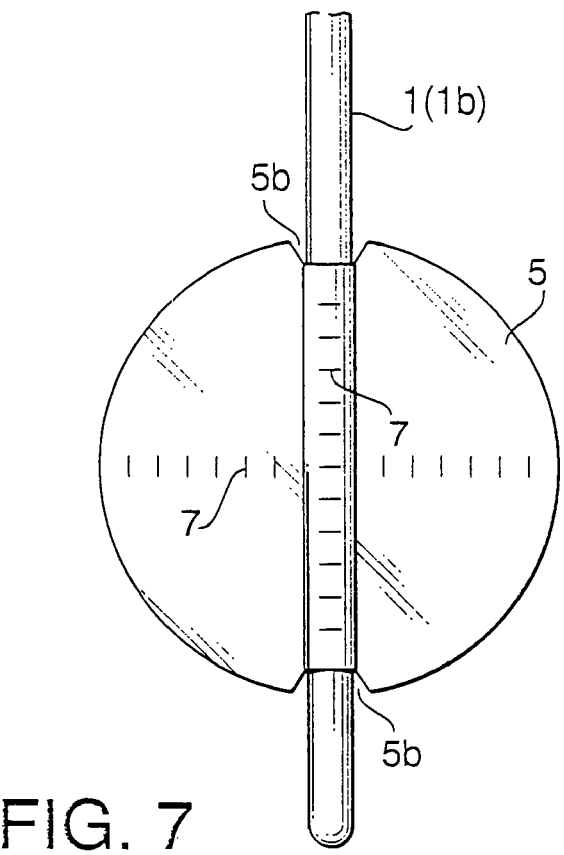
FIG. 7 is a cross-sectional side view of a distal end portion of the measurement tool according to the third embodiment.

Optionally, as shown in FIG. 7, the sheet 5 may be provided with gradations 7. Further optionally, the cylindrical through opening 5b may be formed to have tapered shape having a larger diameter at the axial end side, so that the sheet 5 can be detached from the bendable portion 1b.

Figure 8:
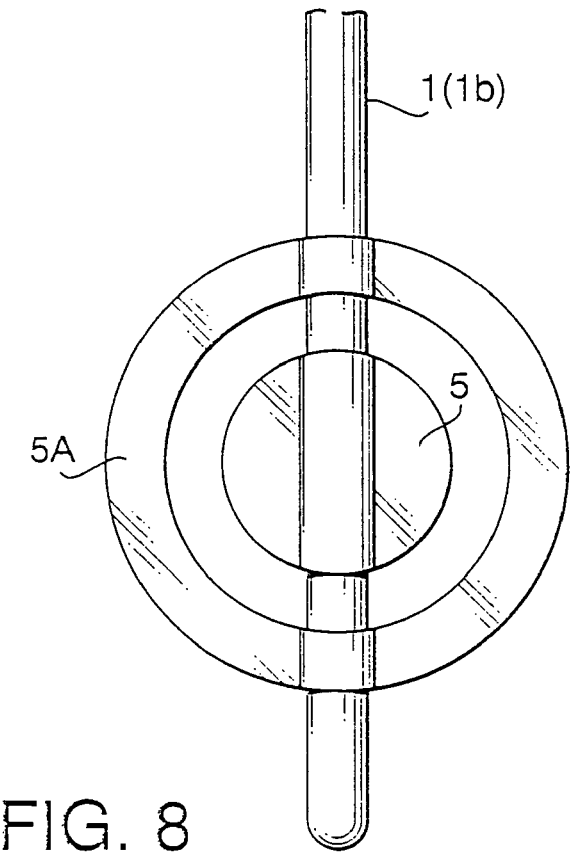
FIG. 8 is a cross-sectional side view of a distal end portion of the measurement tool according to the fourth embodiment.

Still optionally, an annular sheet 5A, which is formed of elastic material, may be provided substantially co-centrically with respect to the sheet 5 (see FIG. 8). With this configuration, a measurable range can be enhanced.

FIFTH-TENTH EMBODIMENTS

Figure 9:
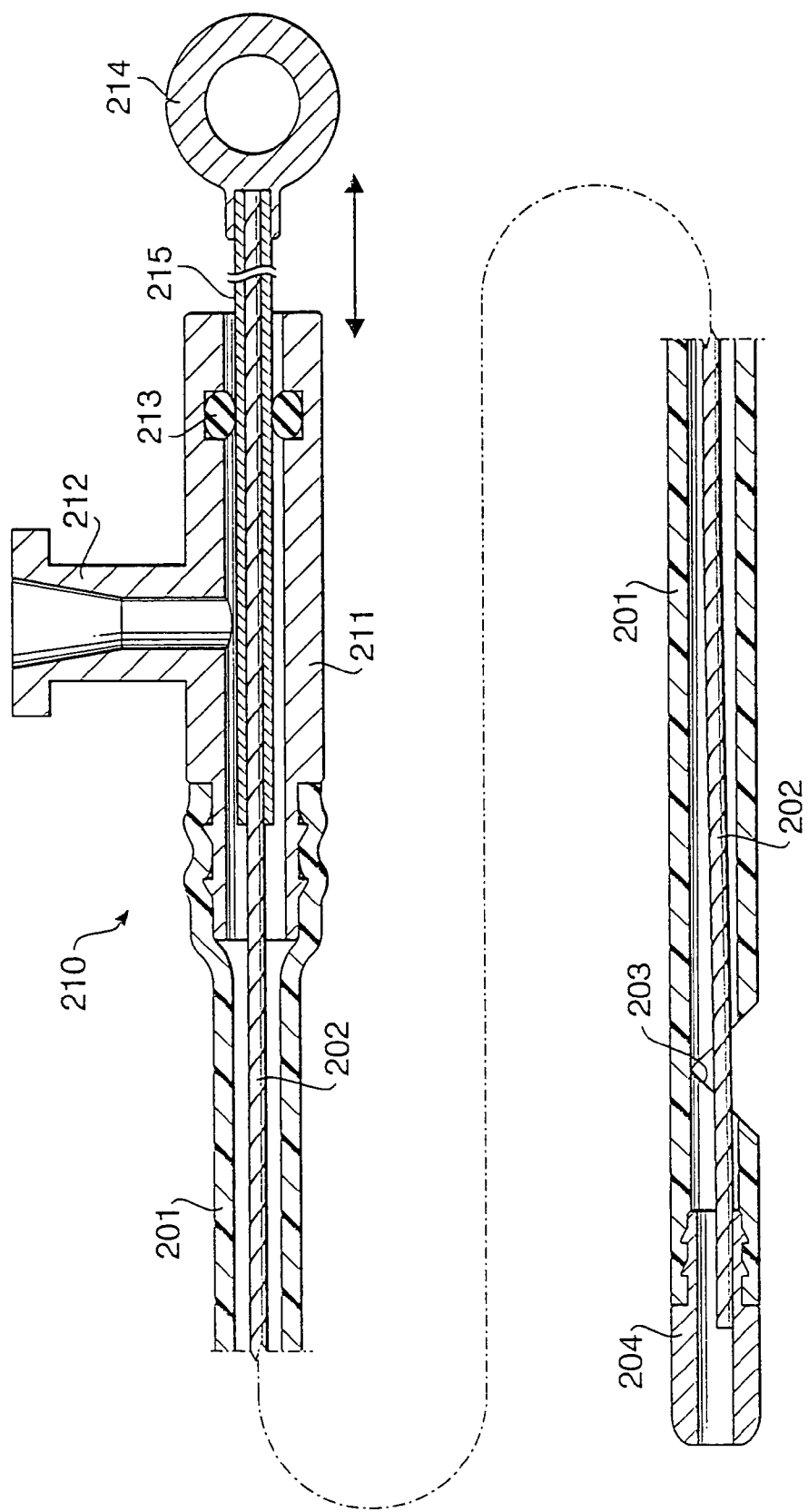
FIG. 9 is a cross-sectional side view of a tubular treatment tool for an endoscope according to a first embodiment of the invention.

FIG. 9 shows a tubular treatment tool for an endoscope according to a first embodiment of the invention.

In FIG. 9, 201 denotes a flexible tube to be inserted in a treatment tool insertion channel. The flexible tube 1 is a tetrafluoroethylene resin tube or polyethylene resin tube, the outer diameter thereof being 1.5 to 2.5 mm, and the length thereof being 1 to 2 meters.

At the tip end portion of the flexible tube 201, a groove 203 having a V-shaped cross section. Inside the flexible tube 1, an operation wire 202 which is formed of, for example, twisted stainless steel wires, are inserted along the axis thereof over the length thereof. The operation wire 202 is movable along the axis of the flexible tube 201.

At the tip end of the flexible tube 201, a metal chip 204 having a through hole in the axial direction is secured. The tip end of the operation wire 202 is secured to the inner circumference of the metal chip 204 by silver brazing or the like. Thus, the tip end of the operation wire 202 is fixed to the tip end portion of the flexible tube 201.

The treatment tool 210 is provided with an operation unit 210. The operation unit 210 includes a main barrel 211 to which the proximal end of the flexible tube 201 is connected. From the main barrel 211, a connection barrel 212 is protruded. By connecting an injector (not shown) to the connection barrel 212, contrast medium or other liquid can be fed through the flexible tube 201. Further, through the flexible tube 201, suction can be done.

The operation wire 202 runs through the main barrel 211, and the rear side end of the main barrel 211 is connected with a finger hook 214. The portion of the operation wire 202 from the main barrel 211 to the finger hook 214, a reinforcement pipe 215 made of stainless steel is provided to cover the operation wire 202.

With the above-described configuration, by moving the finger hook 214 back and forth with respect to the main barrel 11, the operation wire 202 moves back and forth, along the axis, inside the flexible tube 201. In FIG. 9, 213 denotes an O-ring which is used for sealing a space inside the main barrel 211 and outside of the main barrel 211. The O-ring 213 closely contacts the outer circumference of the reinforce pipe 215.

Figure 10:
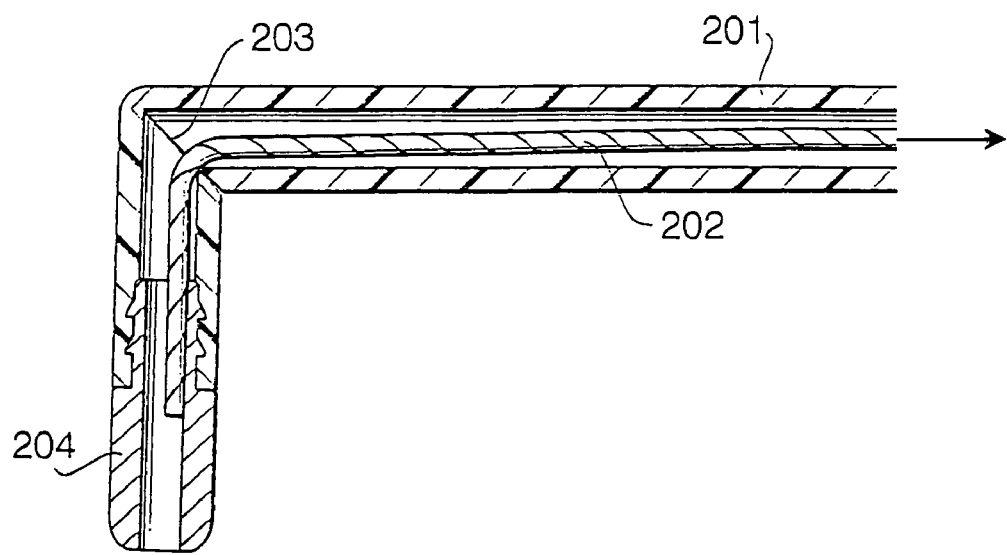
FIG. 10 is a cross-sectional side view of a distal end portion of the tubular treatment tool when the distal end portion is bent.

When the operation wire 202 is pulled (i.e., moved backward) by moving the finger hook 213 in a rear direction (i.e., right-hand side direction in FIG. 9), then, as shown in FIG. 10, the tip end portion of the flexible tube 201 bends toward the groove 203 such that the V-shaped cross section becomes smaller. In an example shown in FIGS. 9 and 10, the maximum bendable angle is set to 90 degrees. It should be noted that the maximum bendable angle is adjusted by setting an angle formed between both sides of the V-shape cross section of the groove 203.

Figure 11:
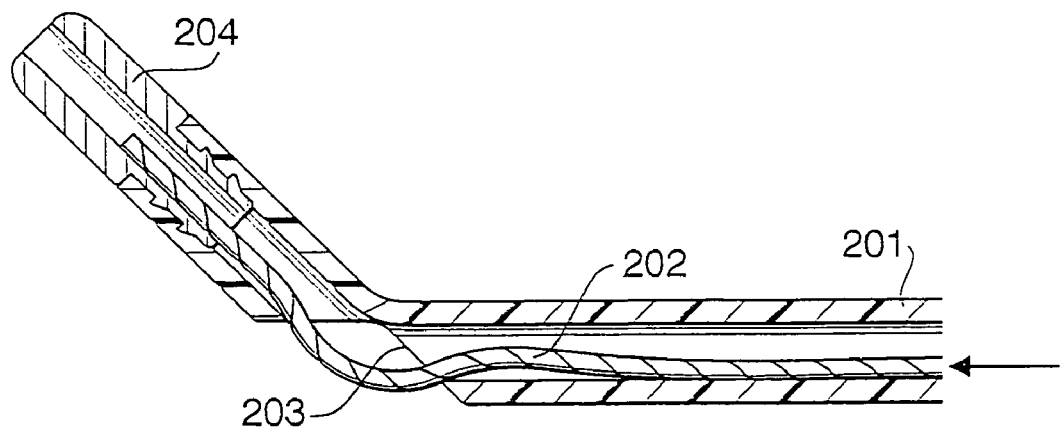
FIG. 11 is a cross-sectional side view of the distal end portion of the tubular treatment tool when the distal end portion is bent in a direction opposite to that shown in FIG. 2.

When the operation wire 202 is pushed (i.e., moved forward) by moving the finger hook 214 in a forward direction (i.e., left-hand side direction in FIG. 9), then, as shown in FIG. 11, the tip end portion of the flexible tube 201 bends in a direction opposite to the groove 203.

Figure 12:
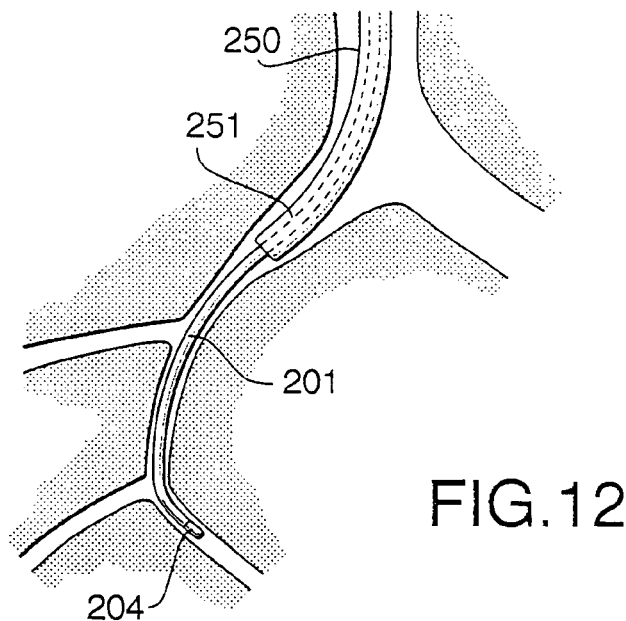
FIG. 12 illustrates the tubular treatment tool in use.

Thus, with the tubular treatment instrument for an endoscope according to this embodiment, the tip end portion (e.g., metal chip 204) of the flexible tube 201, which is protruded from the distal end of the insertion channel 251 of an endoscope 60 (see FIG. 12), can be bent in a desired direction so that the tip end portion can be inserted in a branch tube located at a relatively deep level of bronchial tubes or a bile duct. Generally, such portions cannot be observed by eyes, and contrast medium may be injected and X-ray observation may be performed.

The present invention is not limited to above-described configuration, and may be modified in various ways. For example, the metal chip 204 may be secured to the tip end of the operation wire 202 in various ways.

Figure 13:
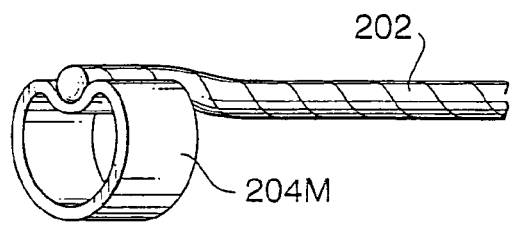
FIG. 13 shows an operation wire fixing structure of a tubular treatment tool according to a second embodiment.

In FIG. 13, a metal chip 204M is formed to have a heart shape, and the tip end of the operation wire 202 is secured at the concave portion of the outer surface of the metal chip 4M. Then, the metal chip 204M, together with the operation wire 202, is press-fixed inside the tip end portion of the flexible tube 1.

Figure 14:
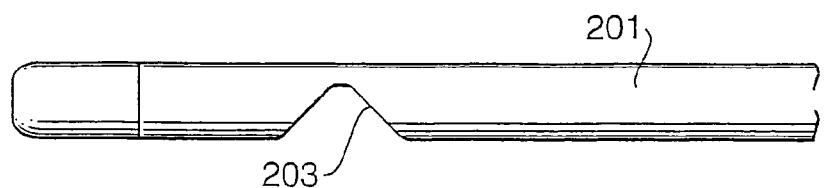
FIG. 14 shows a groove of a tubular treatment tool according to a third embodiment of the invention.

In FIG. 14, a modification of the groove 203 is shown. In this modification, the cross-sectional shape of the groove 203 is modified such that the summit of the upended V-shape has a predetermined length of a level portion. With this configuration, the flexible tube 201 may easily bend in response to operation of the operation wire 202.

In FIG. 15, the groove 203 is formed such that an operation unit side of the V-shaped cross-section inclines steeply, and a tip end side of the V-shaped cross-section gently inclines. With this configuration, when the flexible tube 201 is retracted and the tip end portion of the flexible tube 201 is withdrawn into the treatment tool insertion channel 251, the groove 3 may not be hooked at the end of the treatment tool insertion channel 251.

Figure 17:
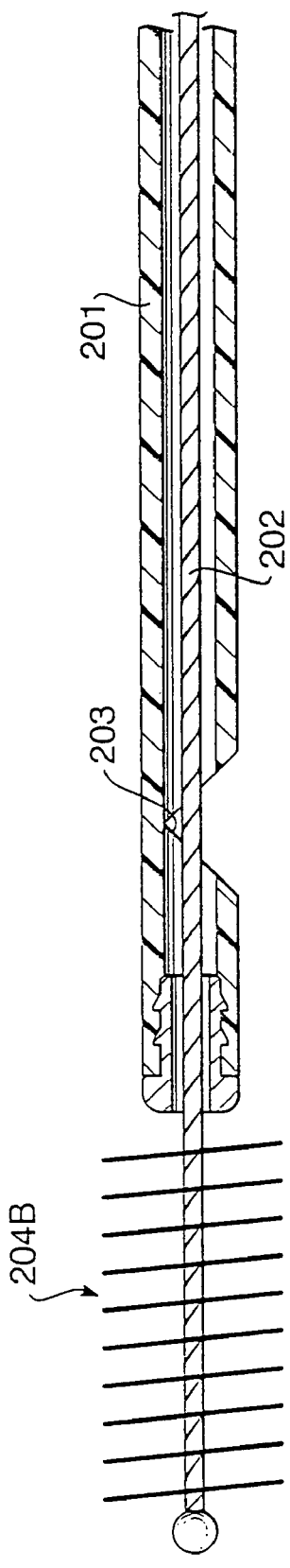
FIG. 17 shows a tubular treatment tool according to a sixth embodiment of the invention, a brush being secured to the tip thereof.

As shown in FIGS. 16 and 17, a spoon tool 204A or a brush tool 204B may be secured instead of the metal chip 204. With such configurations, tissues can be endoscopically collected from the branch tube located at deep inside the bile duct or bronchial tubes.

Also in such a case, by injecting contrast medium through the connection barrel 212, the flexible tube 201 can be inserted into a desired tube, which cannot be observed by eyes, with monitoring X-ray images.

The tools for collecting tissues are generally provided with a sheath made from metal coil having a tendency to be straighten. By employing the above configurations as shown in FIGS. 16 and 17, the flexible tube 201 can be inserted easily since it follows the curvature of the bile duct or bronchial tubes, and therefore, the flexible tube 201 can be inserted into a deep portion.

ELEVENTH-THIRTEENTH EMBODIMENTS

Figure 18:
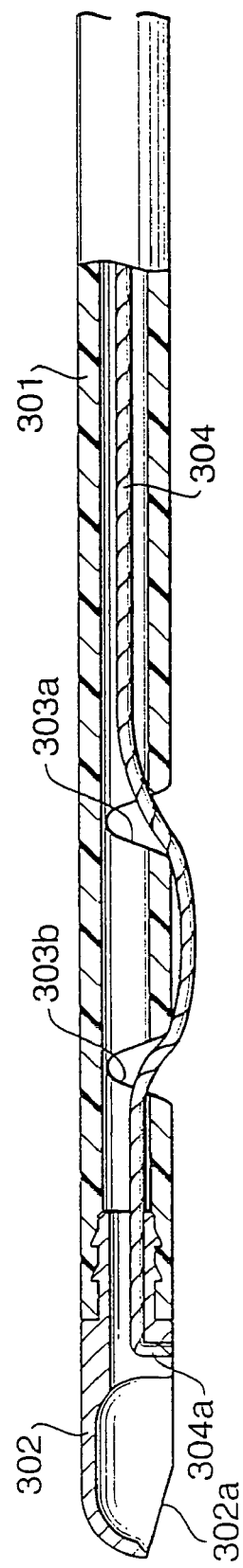
FIG. 18 is a cross-sectional side view of a distal end portion of a bendable treatment tool according to a first embodiment of the invention.

FIG. 18 is a cross-sectional side view of a distal end portion of a bendable treatment tool according to a first embodiment of the invention.

In FIG. 18, numeral 301 denotes a flexible tube, which is to be inserted in a treatment tool insertion channel. At the distal end of the flexible tube 301, a spoon tool 302, which is formed with a cutting edge at the peripheral thereof, for collecting human tissues is secured.

As the flexible tube 301, tetrafluoroethylene resin tube or polyethylene tube may be used. An outer diameter of the flexible tube is approximately 1.5-2.5 mm and the length is 1-2 m.

At the distal end portion of the flexible tube 301, a pair of grooves 303a and 303b, each having a V-shaped cross-section and extending in a direction perpendicular to the axis of the flexible tube 301, are formed with a predetermined interval therebetween along the axis of the flexible tube 301.

Inside the flexible tube 301, an operation wire 304, which is formed from twisted stainless-steel wires, is inserted over the entire length of the flexible tube 301. The operation wire 304 is movable back and forth along the axis of the flexible tube 301. The operation wire 304 can be operated arbitrarily from a proximal end (i.e., right-hand side in FIG. 18) thereof.

The distal end 304a of the operation wire 304 is secured to the spoon tool by brazing or the like, thereby the distal end 4a of the wire 304 is secured to the distal end of the flexible tube 301. It should be noted that the distal end 304a of the wire 304 may be directly secured onto the distal end of the flexible tube 301.

As shown in FIG. 18, the operation wire 304 runs out through the groove 303a and enters inside the flexible tube 301 through the groove 303b. Between the grooves 303a and 303b, the operation wire 304 runs along the outer circumference of the flexible tube 301.

Figure 19:
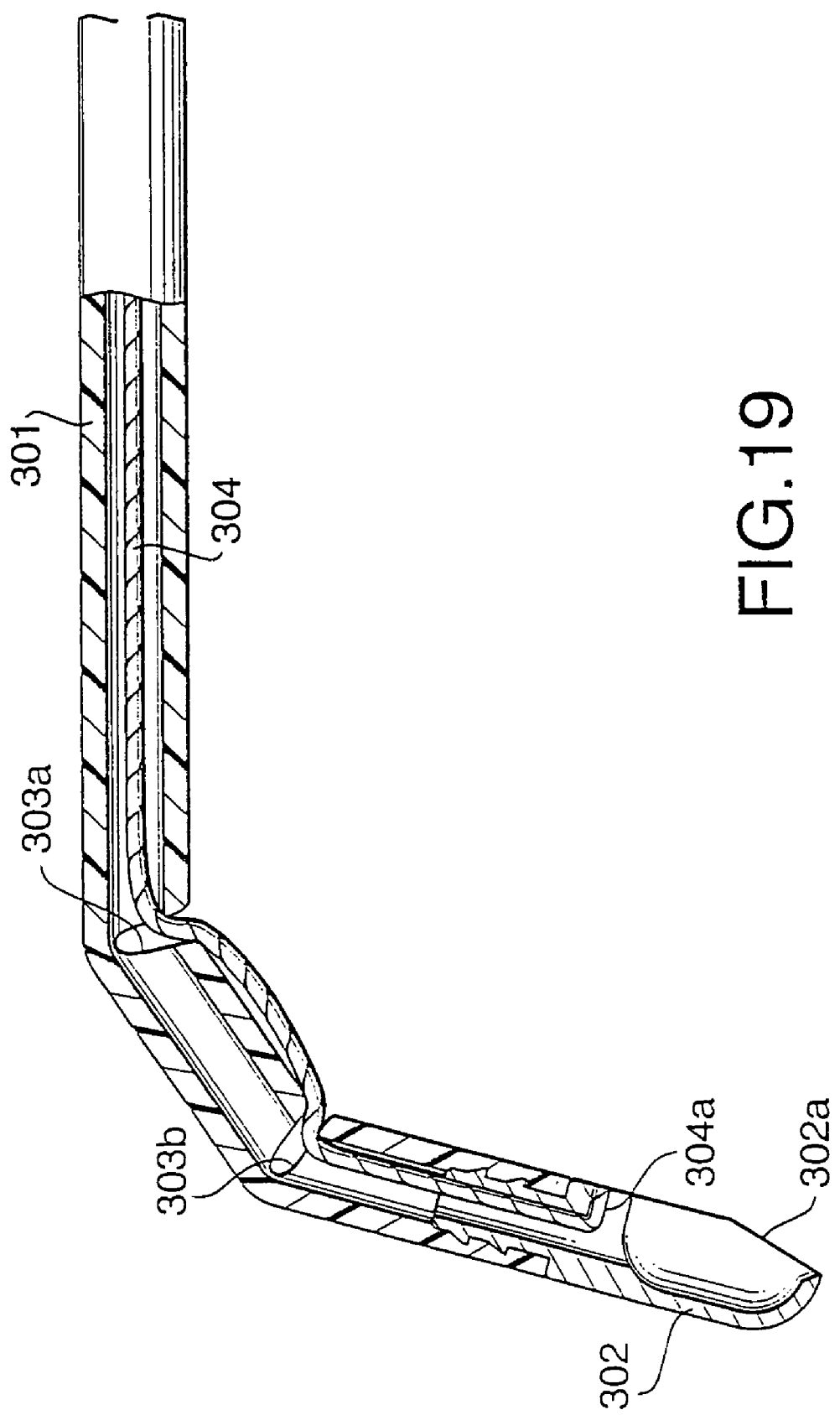
FIG. 19 is a cross-sectional side view of the distal end portion of the bendable treatment tool according to the first embodiment when the distal end portion is bent in one direction.

When the operation wire 304 is pulled at the proximal end side thereof (i.e., moved in the right-hand side in FIG. 18), as shown in FIG. 19, the distal end portion of the flexible tube 1 bends at the grooves 303a and 303b in a direction of a tissue-collecting surface 302a side of the spoon tool 302.

Figure 20:
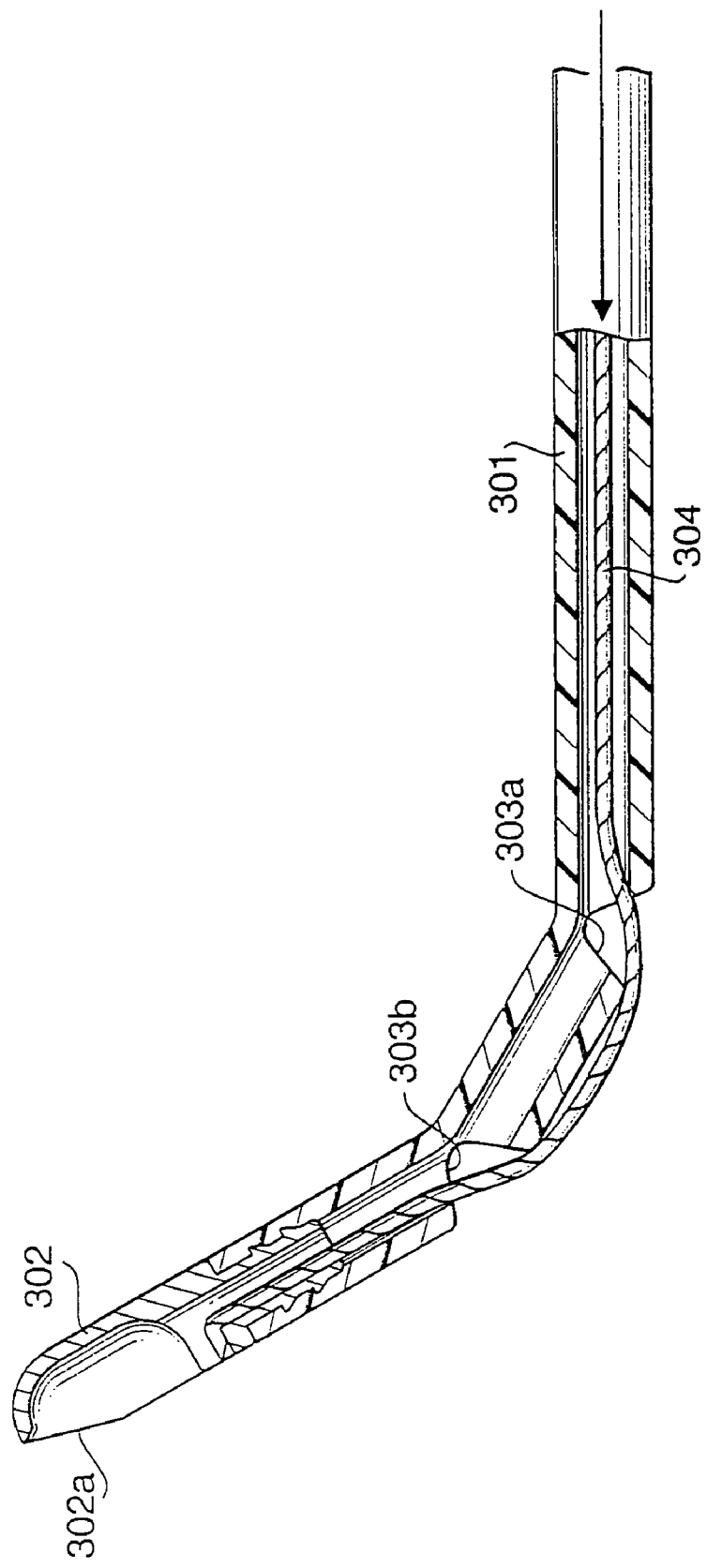
FIG. 20 is a cross-sectional side view of the distal end portion of the bendable treatment tool according to the first embodiment when the distal end portion is bent in another direction.

When the operation wire 304 is pushed at the proximal end side (i.e., moved in the left-hand side direction in FIG. 1), as shown in FIG. 20, the distal end portion of the flexible tube 1 bends, at the grooves 303a and 303b, in a direction opposite to the tissue-collecting surface 302a of the spoon tool 302.

As described above, according to the embodiment, only by forming a pair of grooves 303a and 303b, the distal end portion of the flexible tube 301 can be made bendable, without employing link members as in the conventional art.

FIG. 21 is a cross-sectional side view of a distal end portion of a bendable treatment tool according to a second embodiment of the invention. In this embodiment, two pairs of the grooves 303a and 303b are formed. The operation wire 304 is lead out from the grooves 303a and inserted inside the flexible tube 301 through the grooves 303b. By forming a plurality of pairs of grooves 303a and 303b, the distal end portion of the flexible tube 301 can be bent smoothly at a relatively large radius of curvature.

FIG. 22 is a side view of a distal end portion of a bendable treatment tool according to a third embodiment of the invention. In the third embodiment, at the distal end of the flexible tube 301, a brush tool 312 is secured for collecting the human tissues. Further, in the third embodiment, the two pairs of the grooves 303a and 303b are formed at different positions along the circumferential direction of the flexible tube 301.

Figure 23:
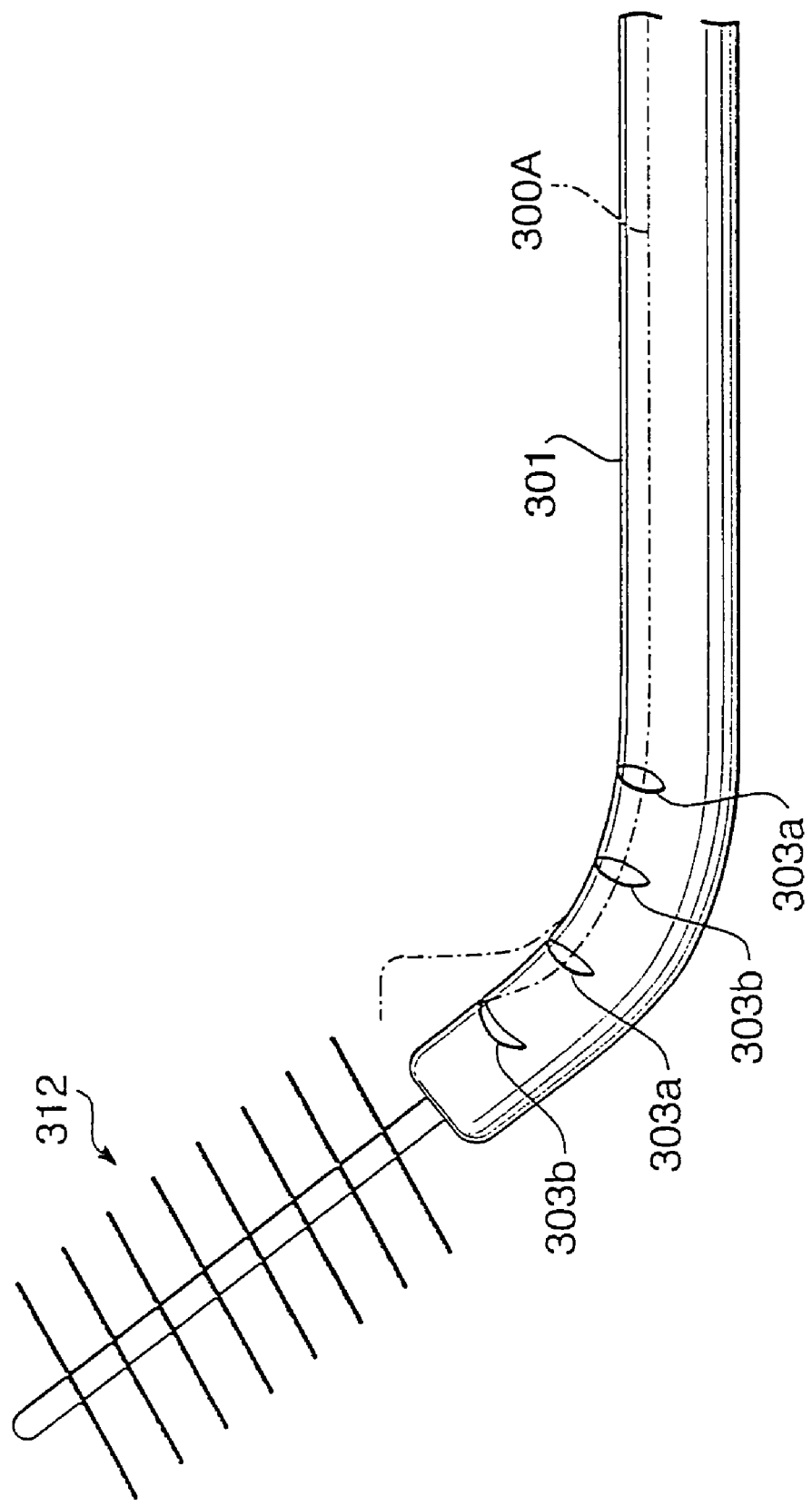
FIG. 23 is a side view of the distal end portion of the bendable treatment tool according to the third embodiment when the distal end portion is bent.

According to this embodiment, if the operation wire 304 is pulled (i.e., moved in the right-hand side in FIG. 22), the distal end portion of the flexible tube 1 is bent in a twisted direction as shown in FIG. 23 (the operation wire 304 is omitted from the drawing for the sake of simplicity). Thus, the distal end portion of the flexible tube 301 may be smoothly inserted in a three-dimensionally curved organs such as a deep portion of a bronchial tube.

FOURTEENTH-SEVENTEENTH EMBODIMENTS

Figure 24:
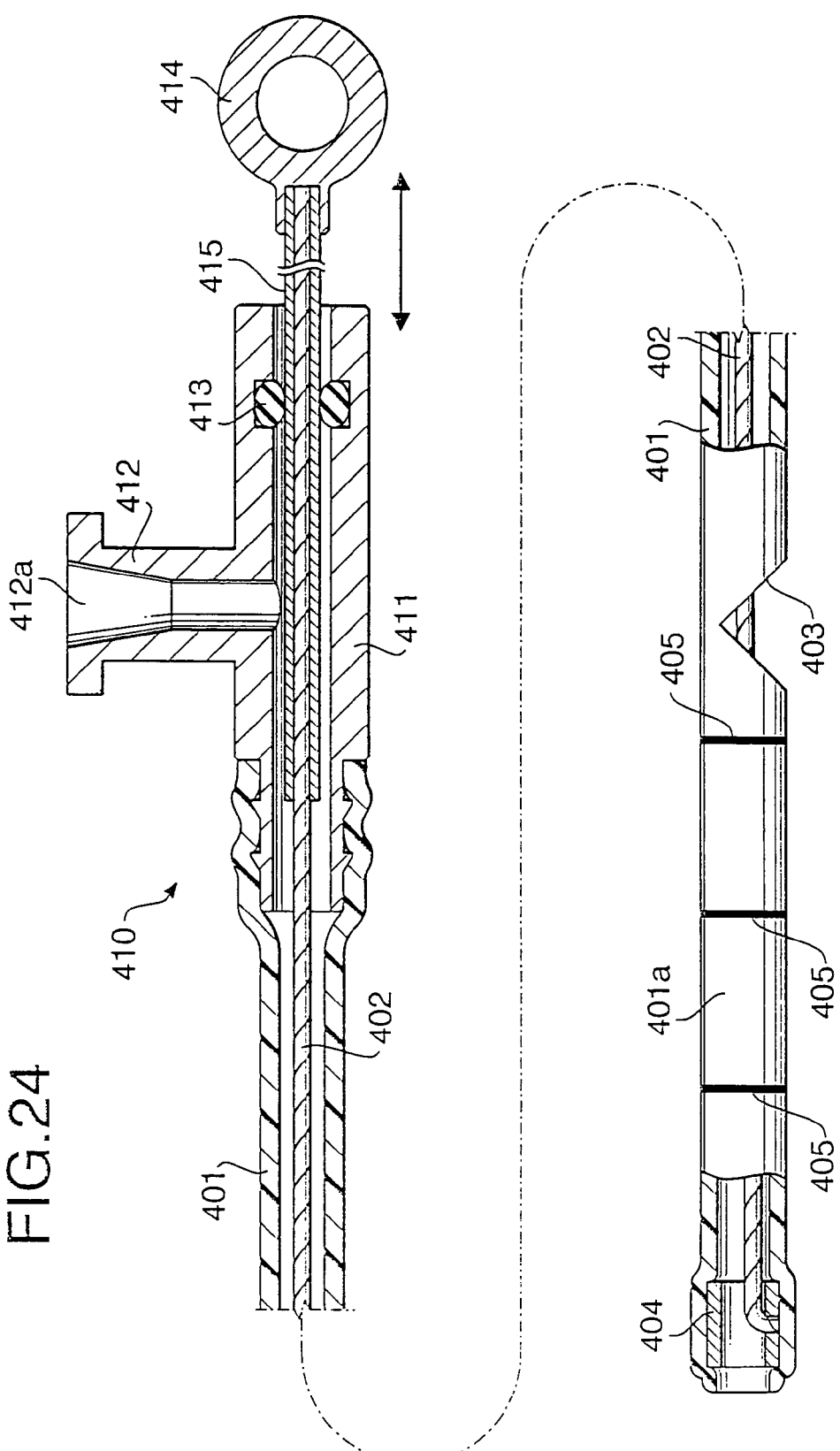
FIG. 24 is a partially cross-sectional side view of a measurement tool for an endoscope according to a first embodiment of the invention.

FIG. 24 is a partially cross-sectional side view of a measurement tool for an endoscope according to a first embodiment of the invention.

In FIG. 24, numeral 401 denotes a flexible tube, which is to be inserted in a treatment tool insertion channel. As the flexible tube 401, tetrafluoroethylene resin tube or polyethylene tube may be used. An outer diameter of the flexible tube is approximately 1.5-2.5 mm and the length is 1-2 m.

On a rear side with respect to the distal end of the flexible tube 401 by 10-50 mm, a groove 403 traversing the flexible tube 1 in the diameter direction, and having a V-shaped cross section is formed. Inside the flexible tube 1, an operation wire 402 formed of twisted stainless steel wires are inserted over the entire length thereof. The operation wire 402 is movable in the axis of the flexible tube 401.

At the distal end of the flexible tube 401, a cylindrical metal chip 404 having a through hole in the axial direction is secured. The distal end of the operation wire 402 is silver brazed to the metal chip 404, thereby the distal end of the operation wire 402 is secured to the distal end of the flexible tube 401. It should be noted that the above structure is an exemplary structure, and the distal end of the operation wire 402 may be secured to the flexible tube 401 at any position on the distal end side with respect to the groove 403.

On the outer surface of the flexible tube 401 on the distal end side portion 401a with respect to the groove 403, circular gradations 405 are formed at a predetermined interval of, for example, 5 mm. Preferably, the graduations 405 are formed to have a color (e.g., blue) which can be clearly distinguished from the mucous membrane.

The proximal end of the flexible tube 401 is connected with an operation unit 410. Specifically, the operation unit includes a main barrel 411 which is connected with the flexible tube 401. On a side portion of the main barrel 411, a connection barrel 412 is protruded. The connection barrel 412 communicates with the flexible tube 401, and a end portion of the connection barrel 412 defines an injection mouth 412a. With this configuration, by connecting an injector or the like (not shown) to the connection barrel 412, through which water or any other liquid can be fed in the flexible tube 401. Further, suction can be performed through the flexible tube 401 and the connection barrel 412.

The operation wire 402 runs straight through the main barrel 411, and the proximal end of the operation wire 402 is connected with a finger hook 414. The portion of the operation wire 402 from the main barrel 411 to the finger hook 414, a stainless-steel reinforcement pipe 415 is provided to cover the operation wire 402 to prevent the same from bending.

With the above-described configuration, by moving the finger hook 414 back and forth with respect to the main barrel 11, the operation wire 402 moves back and forth, along the axis, inside the flexible tube 401. In FIG. 24, 413 denotes an O-ring which is used for sealing a space inside the main barrel 411 and outside of the main barrel 411. The O-ring 413 closely contacts the outer circumference of the reinforcement pipe 415.

Figure 25:
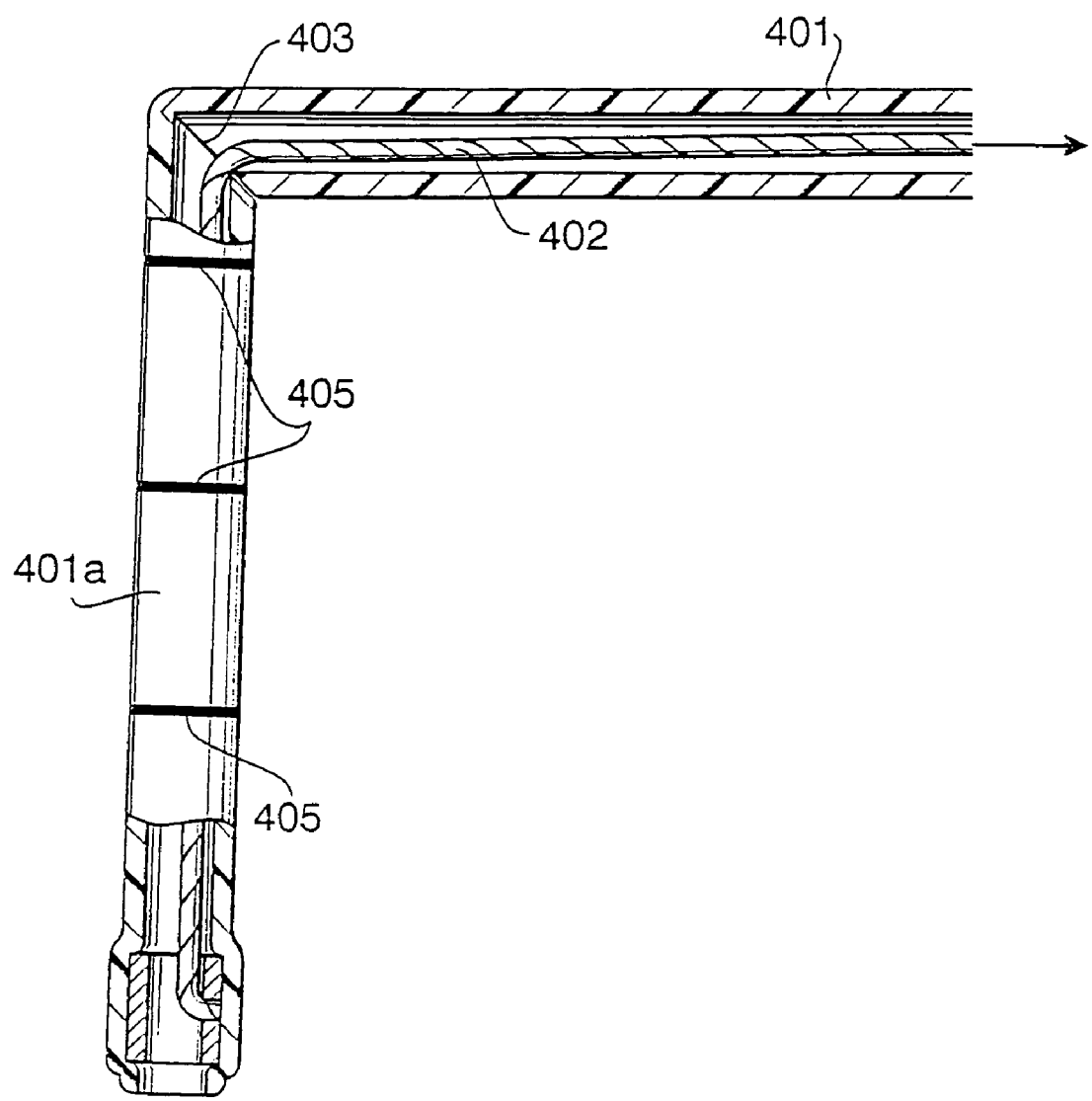
FIG. 25 is a partially cross-sectional side view of a distal end portion of the measurement tool according to the first embodiment, when the distal end portion is bent.

With the above-described configuration, by moving the finger hook 414 back and forth with respect to the main barrel 411, as shown in FIG. 25, the distal end portion 401a of the flexible tube 401 is bent on the groove 403 side at the groove 403. The maximum bending angle of the distal end portion 401a can be adjusted by the cross-sectional shape of the groove 403.

Figure 26:
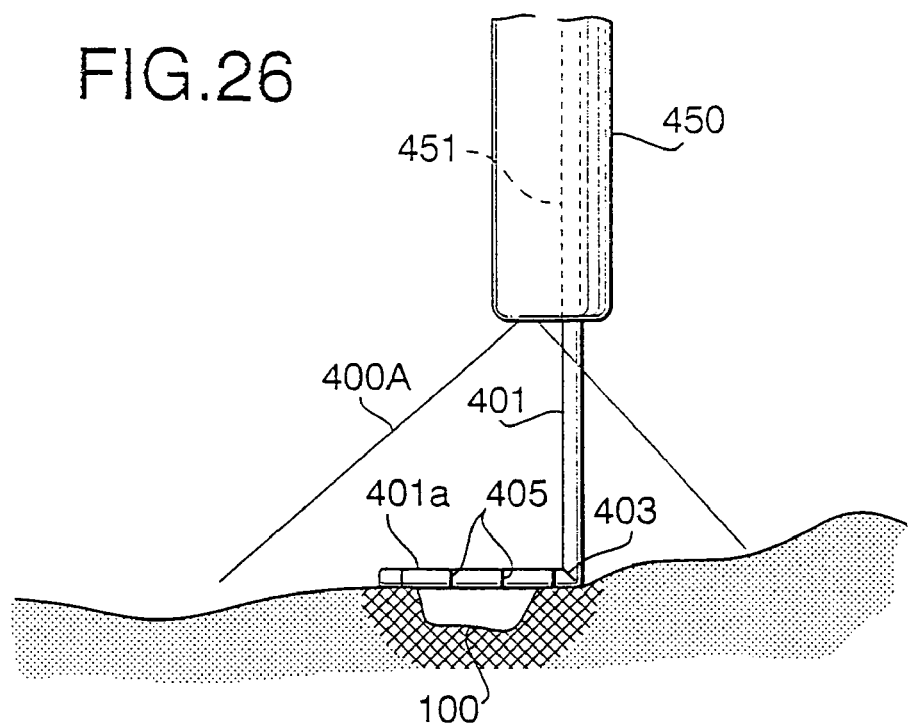
FIG. 26 shows the measurement tool according to the first embodiment, when in use.

As shown in FIG. 26, by making the distal end portion 401a from the insertion channel 451 of the endoscope 450, and bending the distal end portion 401a aside, the graduations 405 can be observed in an observation field A. Thus, using the graduations 5, the size of an object such as an ulcer can be measured.

Figure 27:
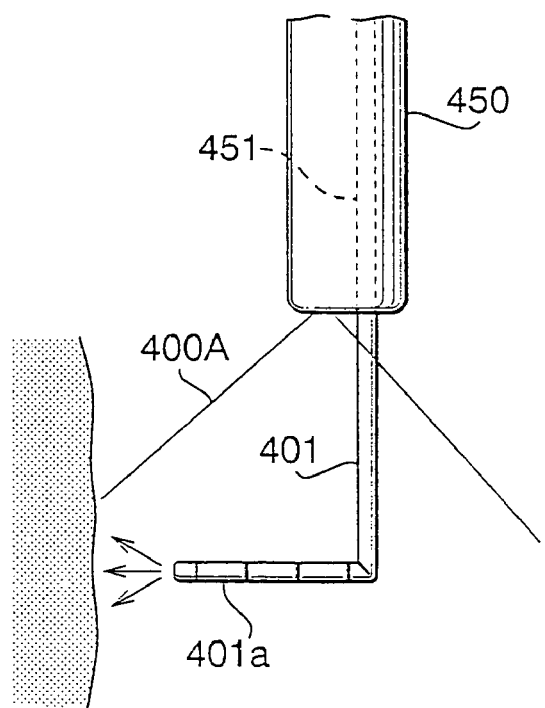
FIG. 27 shows the measurement tool according to the first embodiment when in use.

When necessary, an injector may be connected to the connection barrel 412 to feed water, thereby mucilaginous solution or blood on the mucous membrane can be washed away with the water as shown in FIG. 27.

Figure 28:
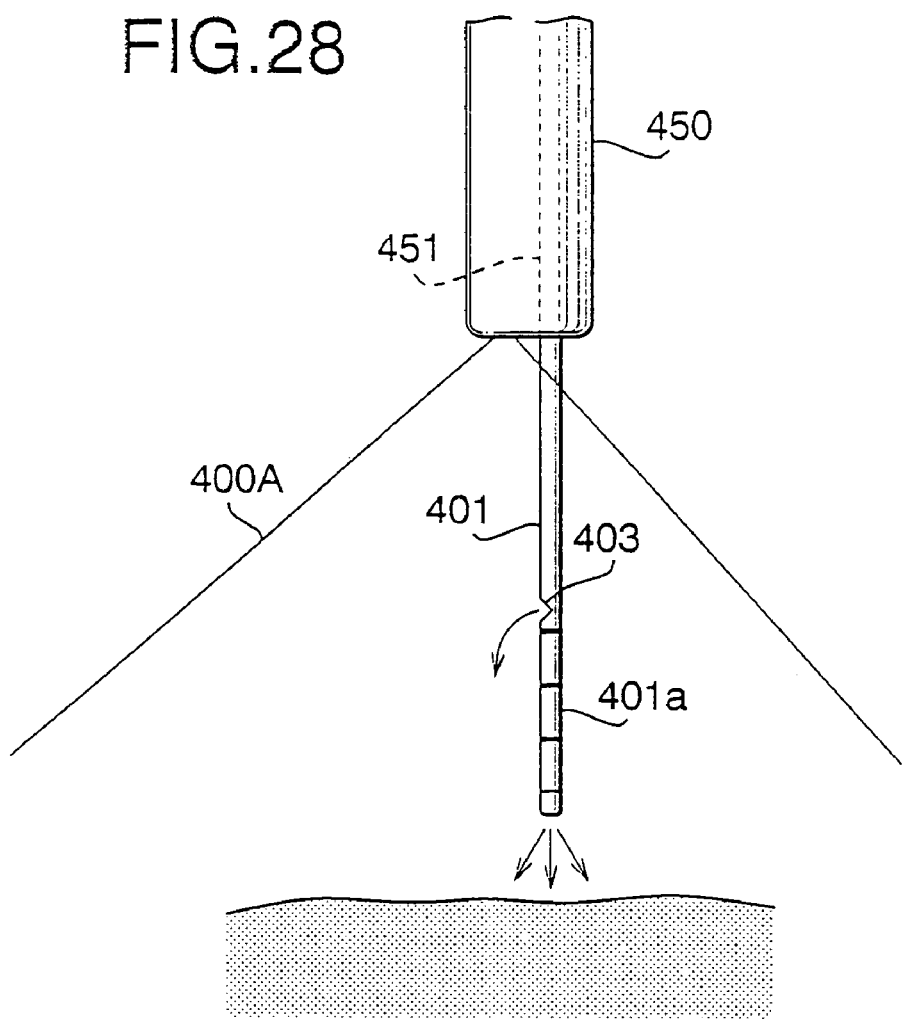
FIG. 28 shows the measurement tool according to the first embodiment when in use.

In this case, if the distal end portion 1a of the flexible tube 401 is straightened as shown in FIG. 28, part of the water may leak from the groove 403. However, most of the water is ejected from the distal end of the flexible tube 401, and the mucilaginous solution or blood will be washed away.

Figure 29:
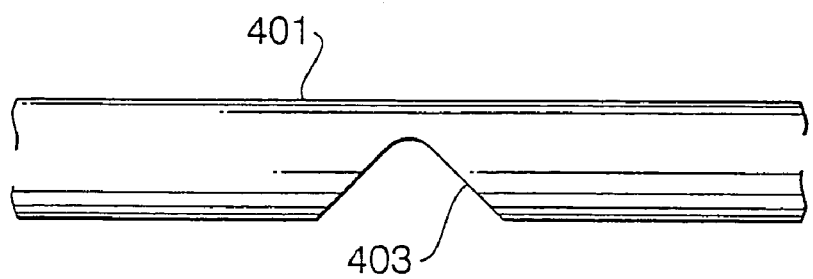
FIG. 29 shows grooves formed on a measurement tool according to a second embodiment.

The present invention is not limited to the above-described configuration, and can by modified in various ways. For example, the groove 403 can be modified such that the bottom of the groove 403 may be formed to have a rounded portion as shown in FIG. 29. With this configuration, the durability against repetitive bending will be improved.

Figure 30:
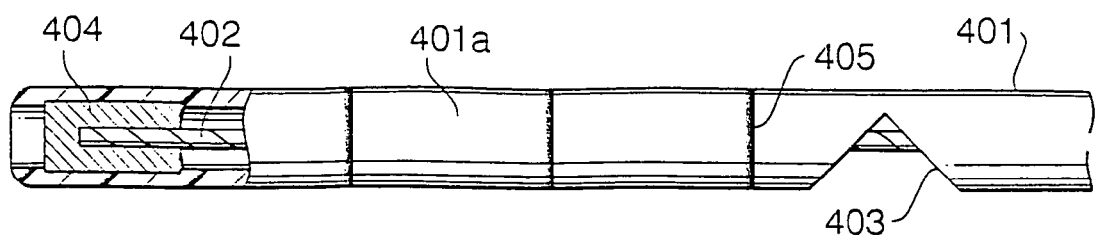
FIG. 30 is a partially cross-sectional side view of a distal end portion of the measurement tool according to a third embodiment.

As shown in FIG. 30, the flexible tube 401 may be configured such that the metal chip 404 completely close the opening of the flexible tube 401 at the distal end thereof. With this configuration, all the liquid fed from the connection barrel 412 will be ejected from the groove 403.

Figure 31:
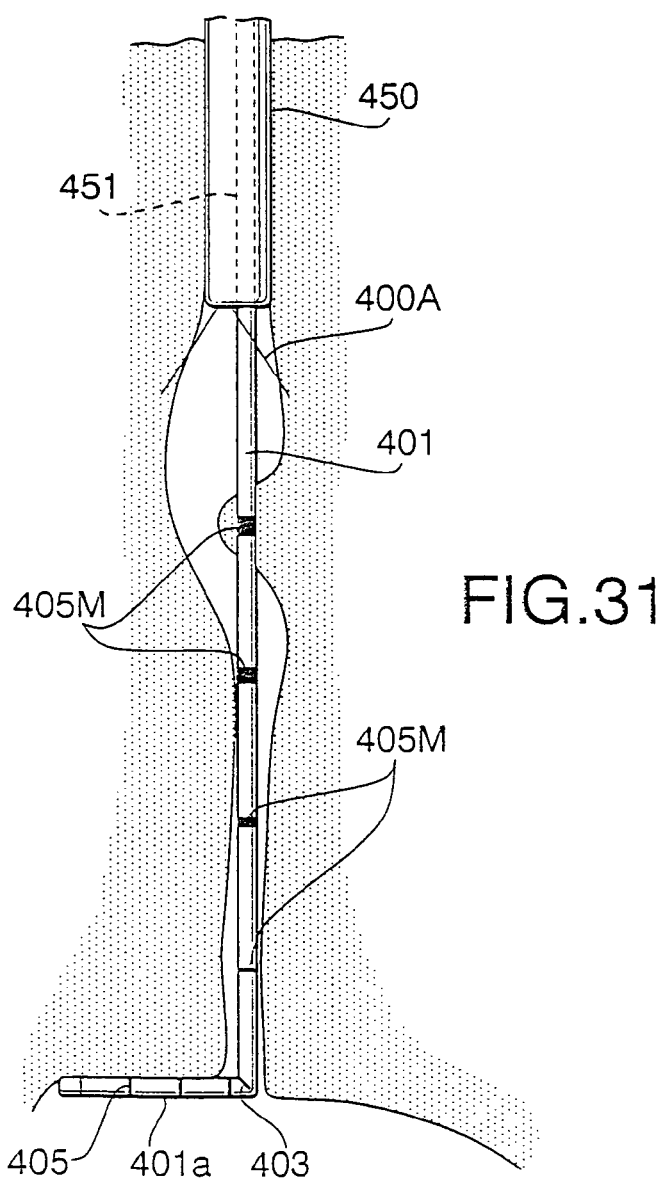
FIG. 31 shows a measurement tool according to a fourth embodiment, when in use.

Optionally, as shown in FIG. 31, graduations 405M may be provided on the outer circumferential of the flexible tube 401 on the rear side with respect to the groove 403. With this configuration, by bending the distal end portion 1a, and a length from the groove 403 to a proximal side portion of a lumen, in which the flexible tube 401 is inserted, can be measured. In this case, if the color and/or thickness and/or number of the graduations at each point is different from the graduation at another point, measurement can be performed easily.

EIGHTEENTH EMBODIMENT

Figures 32, 33:
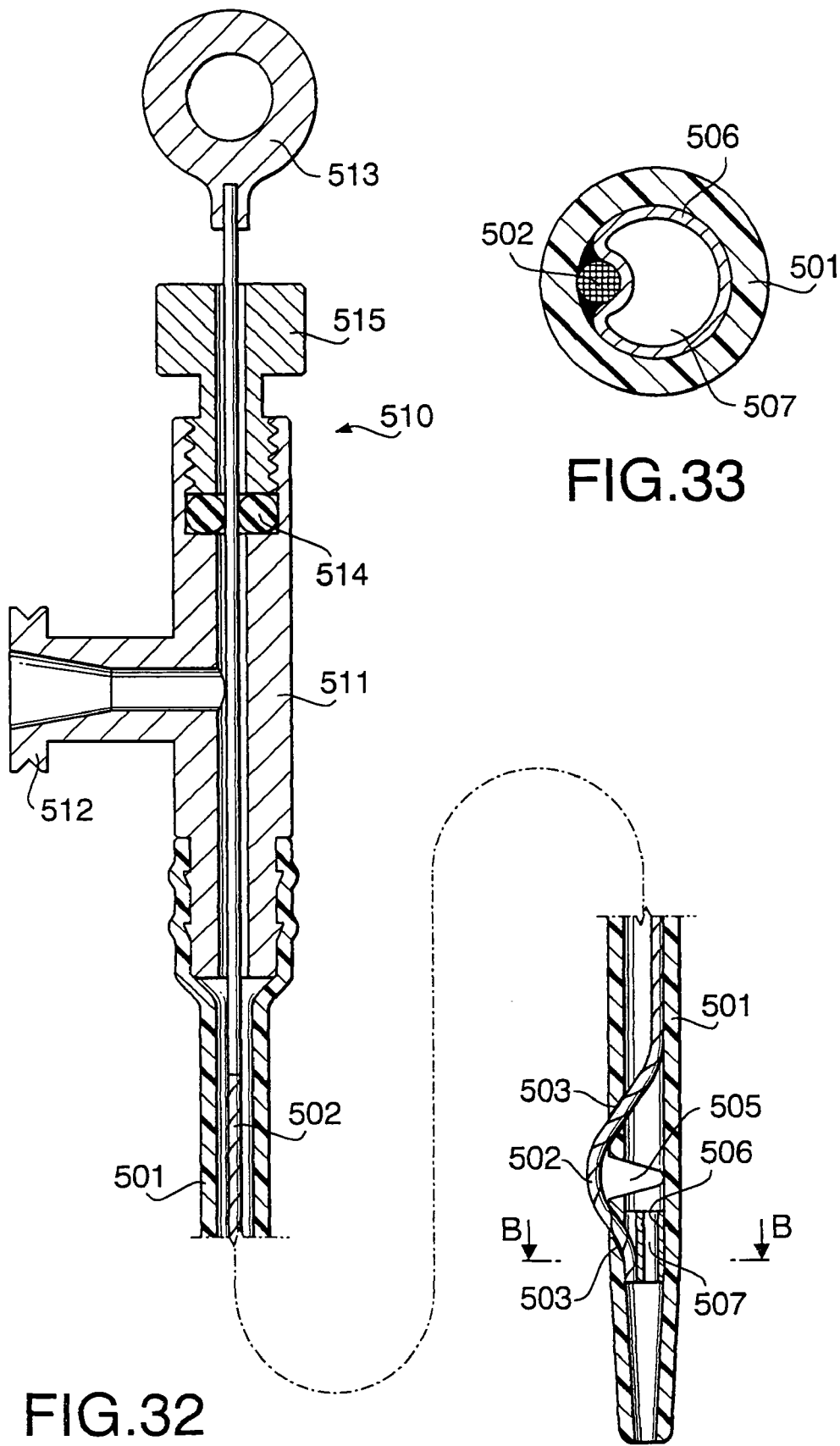
FIG. 32 is a partially cross-sectional side view of a catheter for an endoscope according to a first embodiment of the invention.
FIG. 33 is a cross-sectional view taken along line B-B of FIG. 32.

FIG. 32 is a cross-sectional side view showing an entire structure of a catheter for an endoscope according to a first embodiment of the invention.

The catheter includes a flexible tube 501 which is to be inserted in a treatment tool insertion channel of an endoscope (not shown). The flexible tube 501 is made of tetrafluoroethylene resin, inner/outer diameters of which are approximately 1 mm/2 mm.

Inside the flexible tube 501, an operation wire 502 formed of twisted stainless-steel wires over the entire length of the flexible tube 501. The diameter of the operation wire 502 is sufficiently small so that it does not prevent flow of liquid inside the flexible tube 501. The operation wire 502 is movable along the axis of the flexible tube 501.

At a distal end portion of the flexible tube 501 (i.e., at a position 1-5 cm spaced from the distal end of the flexible tube 1), a groove 505, which extends in a direction perpendicular to the axis of the flexible tube 501 and has a V-shaped cross section, is formed. The depth of the groove 505 is set to traverse the inner diameter, and thus, the thickness of the flexible tube 1 remains without being formed with groove 505.

Further, the bottom of the groove 505 is formed to have a curved surface. Therefore, the flexible tube 501 may not be cracked even if it is bent at the groove repeatedly. A pair of holes 503 are formed on the flexible tube 501 with the groove 504 located therebetween. The operation wire 502 is inserted through the holes 503 so that the operation wire 502 is located outside the flexible tube 501 at a portion between the two holes 503.

The distal end of the operation wire 502 is silver brazed to a stopper 506 which is made of, for example, stainless-steel. The stopper 506 is provided at a position on the distal end side of the groove 505 of the flexible tube 501.

FIG. 33 is a cross-sectional view of the stopper 506 taken along line B-B of FIG. 32. The stopper 506 is a pipe member which is inscribed in the flexible tube 501. A portion of the stopper 506 at which the operation wire 2 is secured is formed as a concave portion, and a liquid flowing path 507 is defined in the axial direction thereof.

As shown in FIG. 32, the distal end portion of the flexible tube 1 is configured such that the distal end side with respect to the stopper 506 is tapered to have a smaller diameter at the portion closer to the end. With this configuration, the stopper 6 does not move freely to the distal end portion. Accordingly, the stopper 506 is fixed in the flexible tube 501.

An operation unit 510 is connected to the proximal end of the flexible tube 501. A connection mouth 512 communicating the flexible tube is protruded on a main barrel 511. By connecting an injector of the like to the connection mouth 512, injection of chemicals or suction can be performed. In FIG. 1, 514 denotes an O-ring for sealing. By fastening or releasing a screw 515, the deformation amount of the O-ring 514 can be adjusted.

By moving a finger hook 513, which is connected to the proximal end of the operation wire 502, relative to the main barrel 511, the operation wire 502 moves back and forth along the axis of the flexible tube, thereby the distal end portion of the flexible tube can be bent arbitrarily.

Figure 34:
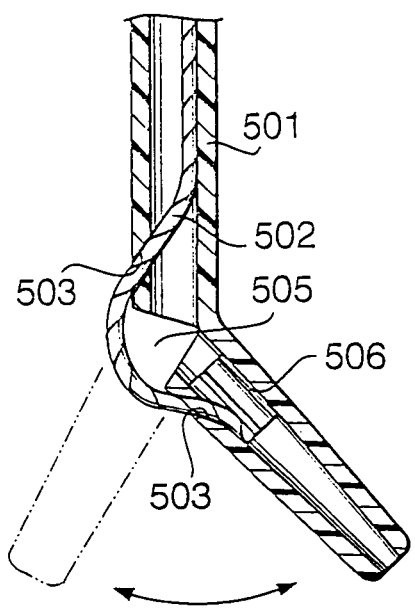
FIG. 34 shows a cross-sectional side view of the catheter according to the first embodiment, when the distal end portion is bent.
Figure 35:
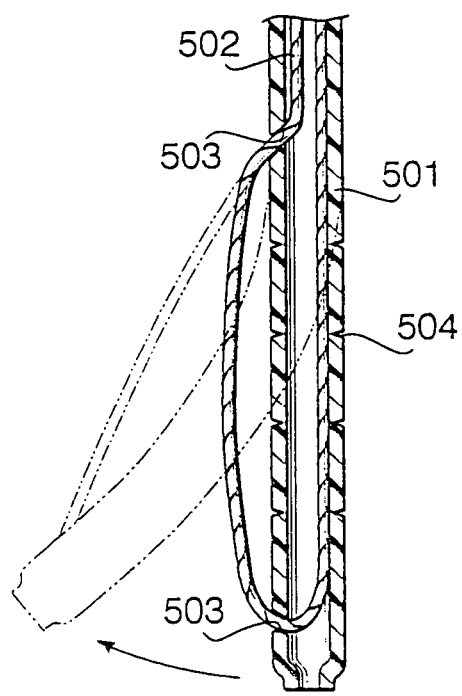
FIG. 35 shows a cross-sectional side view of a conventional catheter when the distal end portion thereof is bent.

FIG. 34 shows a cross-sectional side view of the flexible tube 501. When the operation wire 502 is pulled at the operation unit 510, the distal end portion of the flexible tube 501 bends in a direction where the groove 505 closes, as indicated by dotted lines.

If the operation wire 502 is pushed at the operation unit 510, as shown in FIG. 34, the distal end portion of the flexible tube 1 in a direction where the groove 505 opens wider, as indicated by solid lines in FIG. 34.

With this configuration, a resistive force against the movement of the wire 502 is a force necessary for bending the flexible tube 1 at the groove 505. Thus, even when the operation wire 502 is pushed, the flexible tube 501 can be bent.

As described above, according to the above-described embodiment, the distal end portion of the flexible tube 501 can be bent in both directions at the position where the groove 505 is formed. Therefore, the flexible tube can be directed to the desired position easily.

NINETEENTH AND TWENTIETH EMBODIMENTS

Figure 38:
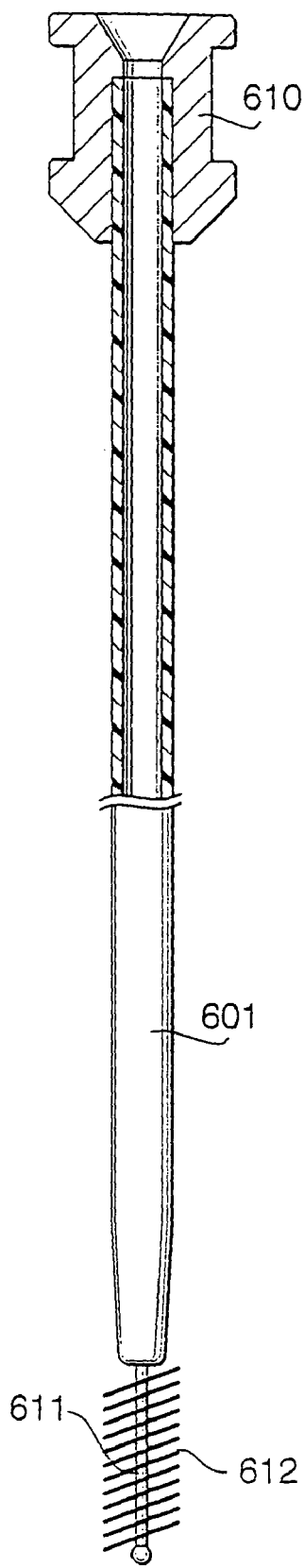
FIG. 38 is a partially cross-sectional side view showing an entire structure of the cytodiagnosis brush according to the first embodiment.

FIG. 38 shows a partially cross-sectional side view of a cytodiagnosis brush for an endoscope according to a first embodiment. In FIG. 38, 601 denotes a flexible tube to be inserted in a treatment tool channel of an endoscope. The flexible tube 601 is made of, for example, tetrafluoroethylene resin.

At the proximal end of the flexible tube 601, a connection mouth piece 610 is connected. At the distal end of the flexible tube 601, a brush shaft 611 provided with radially planted brush 612.

Figure 36:
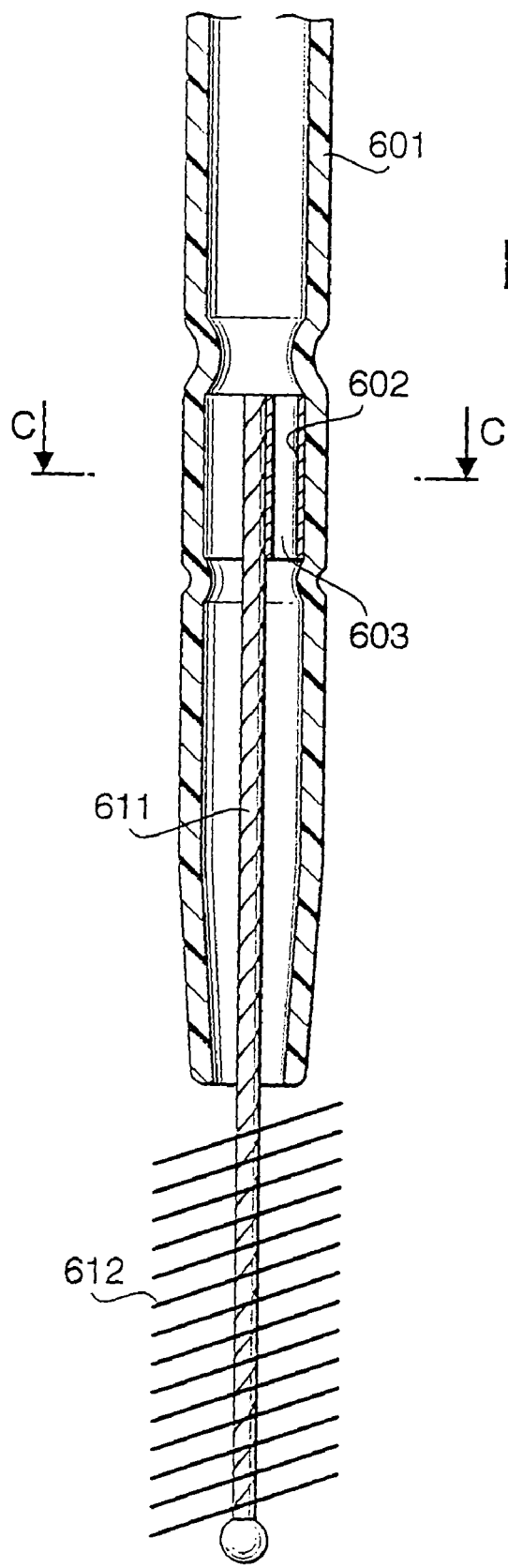
FIG. 36 is a cross-sectional side view of a distal end portion of a cytodiagnosis brush according to a first embodiment of the invention.

FIG. 36 shows a distal end portion of the flexible tube 601. The brush 612 is provided at the distal end portion of the shaft 611, and the remaining portion of the shaft 611 is inserted in the flexible tube 601. The proximal end of the shaft 611 is secured with a stopper 602. The stopper 602 is fixed to the distal end portion of the flexible tube 1 by heat-reducing the diameter of the flexible tube 601 at both sides of the stopper 602.

Figure 37:
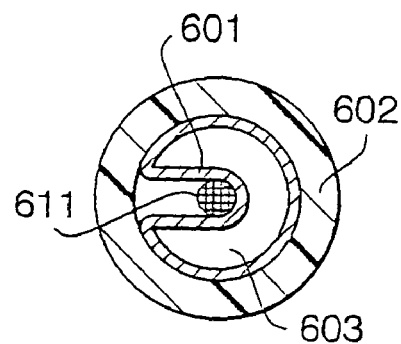
FIG. 37 is a cross-sectional view taken along line C-C of FIG. 36.

FIG. 37 shows a cross-sectional view taken along line C-C of FIG. 36. The stopper 602 is made of a stainless-steel pipe formed with a concave portion, to which the proximal end of the shaft 611 is silver brazed.

An area of the stopper 602, which is not closed by the brush, defines a liquid path 603. That is, the proximal end side of the flexible tube 601 communicates with the distal end side thereof without being closed by the stopper 602.

Thus, when cleaning fluid or disinfecting fluid is injected to the flexible tube 1 through the connection mouth 310, the fluid passes through the liquid path and is fed out of the distal end of the flexible tube 601. Therefore, the flexible tube 601 can be cleaned and/or disinfected over the entire length thereof, reliably and relatively easily.

Figure 39:
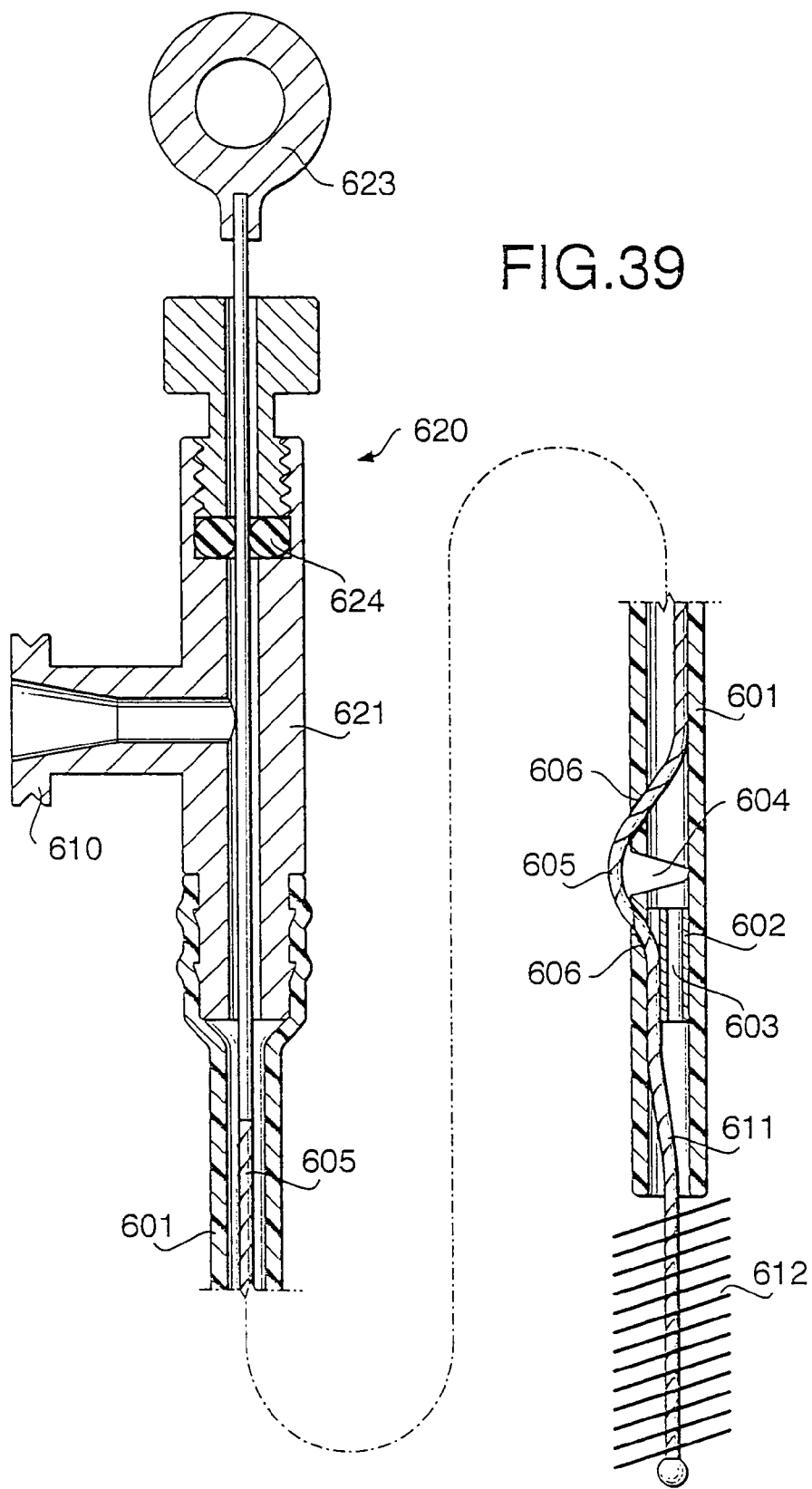
FIG. 39 is a cross-sectional side view showing an entire structure of a cytodiagnosis brush according to a second embodiment.

FIG. 39 shows the cytodiagnosis brush for an endoscope according to a second embodiment. In this embodiment, an operation wire 605 formed of twisted stainless-steel wires are inserted in the flexible tube 601 from the proximal end to the distal end portion thereof.

The operation wire 605 has a sufficiently small diameter in comparison to the inner diameter of the flexible tube 1 so that it does not obstruct the flow of liquid inside the flexible tube 601. The operation wire 5 is movable, in the flexible tube 601, in a direction of the axis of the flexible tube 601.

At a position close to the distal end of the flexible tube 601 (i.e., 1-5 cm from the distal end), a groove 604 having a V-shaped cross section is formed.

The depth of the groove 604 is set to traverse the inner diameter of the flexible tube 601. Thus, a portion of the flexible tube 601 located at the bottom of the V-shaped groove 4 remains uncut. Further, the bottom of the V-shaped groove 604 is formed to have a curved surface but not an edge. Therefore, even if the flexible tube 601 is repeatedly bent at the groove 604, a crack or the like will not be formed on the flexible tube 601.

As shown in FIG. 39, the flexible tube 601 is formed with a pair of holes with the groove 604 located therebetween. The operation wire 605 is inserted through the pair of holes 606 such that the operation wire 605 is located outside the flexible tube 1 between the pair of holes 606.

The distal end of the operation wire 605 is silver brazed to a stopper 602 which is arranged, inside the flexible tube 601, at a position on a distal end side with respect to the groove 604. The proximal end of the shaft 611 of the brush is also silver brazed to the stopper 602.

To the proximal end of the flexible tube 601, an operation unit 620 is connected. The operation unit 620 includes a main body 621 and a connection mouth 10, which communicates with the flexible tube 601, is protruded from the main body 621. By coupling an injector or the like to the connection mouth 610, fluid can be injected inside the flexible tube 601. In FIG. 39, 624 denotes an O-ring for sealing.

The proximal end of the operation wire 605 is connected to a finger hook 623. By moving the finger hook 623 relative to the main body 621, the operation wire 605 can be moved along the axis of the flexible tube 601, thereby bending the distal end portion of the flexible tube 601.

Figure 40:
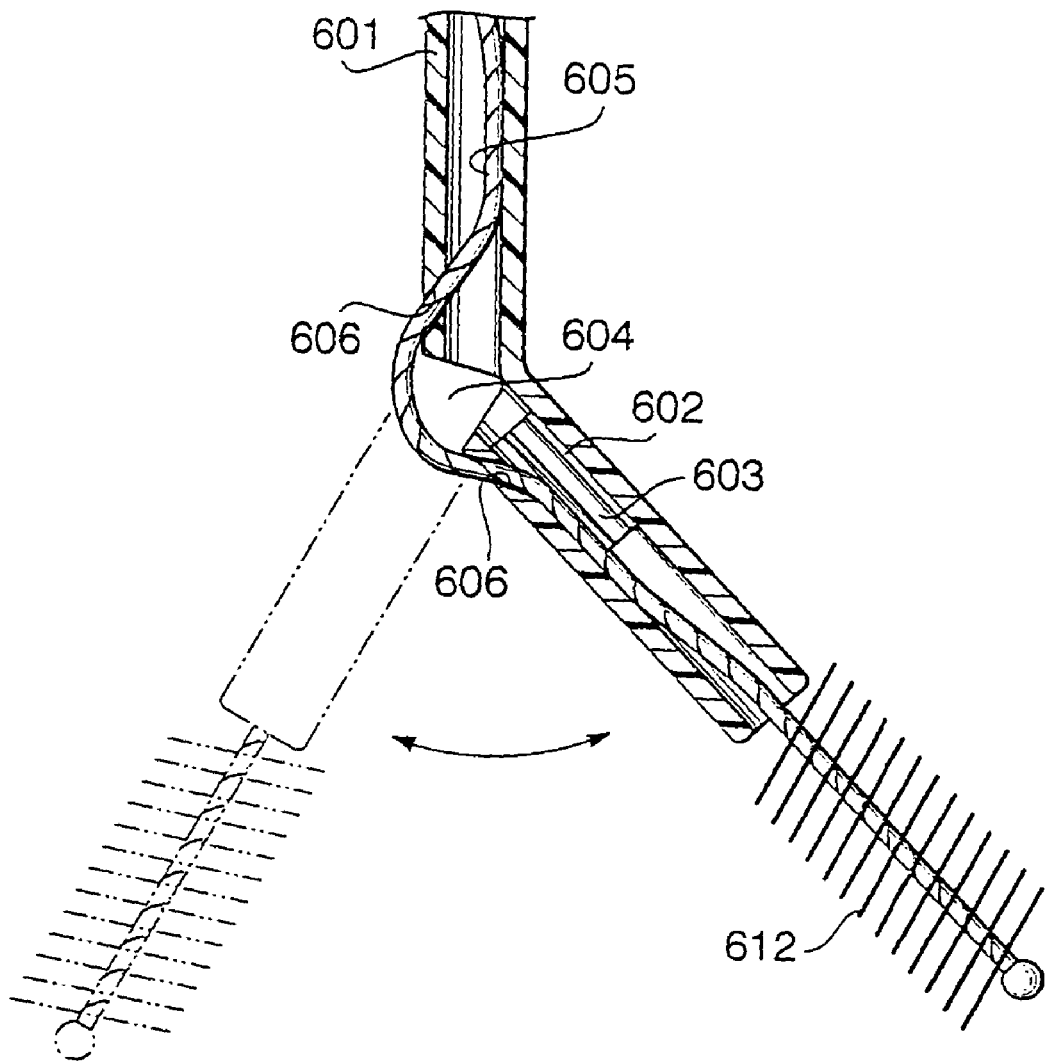
FIG. 40 is a cross-sectional side view of the distal end portion of the cytodiagnosis brush according to the second embodiment.

FIG. 40 shows a cross-sectional view of the distal end portion of the flexible tube 601. When the operation wire 605 is pulled at the operation unit 620, the distal end portion of the flexible tube 601 bends, at the groove 604, in a direction in which the V-shaped groove 604 is closed as indicated by two-dotted lines in FIG. 40.

When the operation wire 5 is pushed at the operation unit 620, the flexible tube 1 is bent in a direction where the V-shaped groove 604 opens wider, as indicated by solid lines in FIG. 40. With this structure, since the liquid path is defined and stopper does not block the flow of fluid, the entire length of the flexible tube 601 can be cleaned and/or disinfected reliably and easily.

It should be noted that above-described structures are examples, and various modification can be made. For example, the stopper 602 may be formed as a hollow cylindrical member, and the shaft of the brush 611 may be secured on the inner surface of the hollow-cylindrical stopper 602.

TWENTY-FIRST AND TWENTY-SECOND EMBODIMENTS

Figure 42:
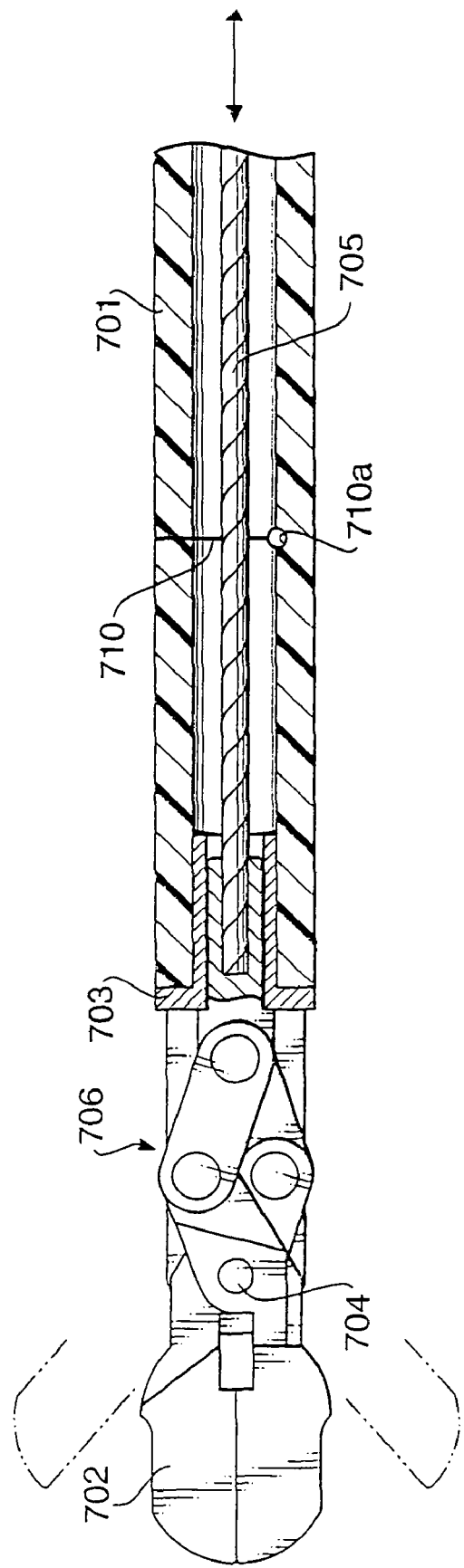
FIG. 42 is a cross-sectional side view showing a distal end portion of a biopsy forceps according to the first embodiment when it is straightened.

FIG. 42 is a cross-sectional side view of a biopsy forceps according to a first embodiment of the invention. The biopsy forceps has a flexible tube 701 made of, for example, tetrafluoroethylene resin.

Inside the flexible tube 701, an operation wire 705 is inserted over the entire length of the flexible tube 701. The operation wire 705 is movable in the flexible tube 701 in the axial direction thereof. Specifically, an operation unit is secured to the proximal end of the flexible tube 701, and the operation wire 705 is operated at the operation unit (not shown).

At the distal end of the flexible tube 701, a support frame 703 is fixed. At the tip portion of the support frame 703, a pair of forceps cups are supported such that they are opened/closed about the rotation shaft 704.

Between the operation wire 705 and the forceps cups 702, a pantograph type link mechanism 706. By operating the operation wire 705, the pair of forceps cups 702 are opened (as indicated by two-dotted lines) or closed (as indicated by solid lines) about the rotation shaft 704.

At a portion close to the distal end of the flexible tube 701 (e.g., several millimeters to ten and several millimeters from the forceps cups), an incision 710 is formed from the outer surface of the flexible tube 701 along its diameter. The end of the incision 710 is located at a position passed through the inside of the flexible tube 701, and the proximal end side portion of the flexible tube 701 and the distal end side portion thereof are connected by the remaining portion of the flexible tube 701 where the incision is formed.

Figure 41:
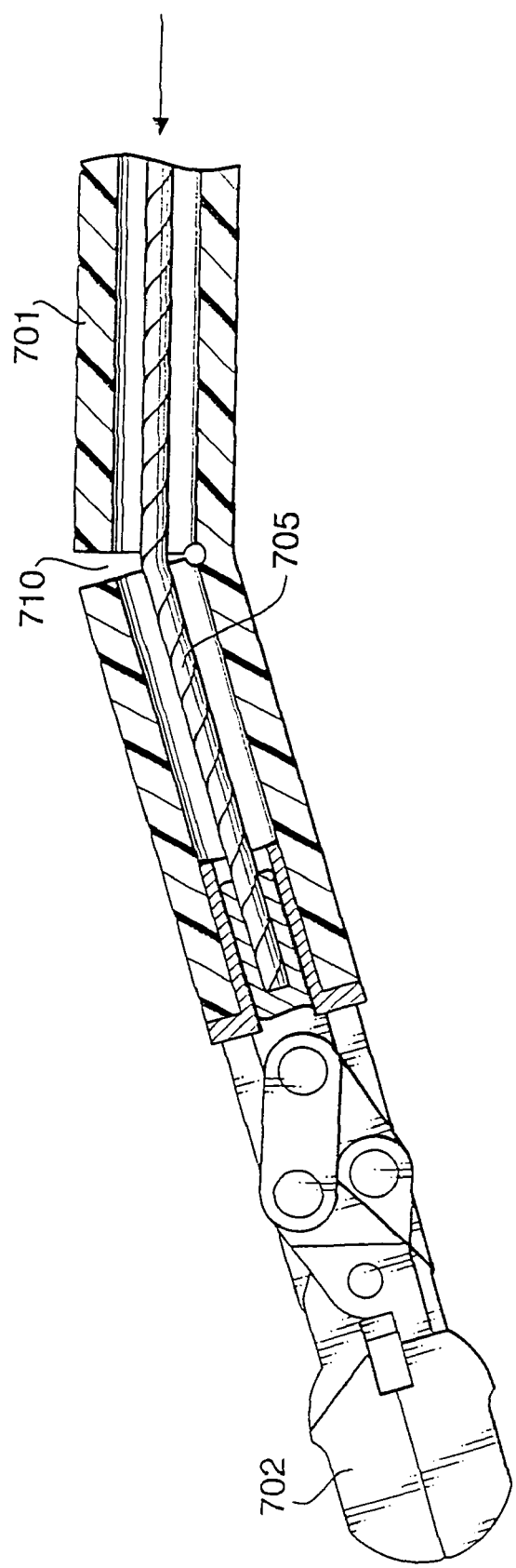
FIG. 41 is a cross-sectional side view showing a distal end portion of a biopsy forceps according to a first embodiment when it is bent.

When the operation wire 5 is pushed at the operation unit, the force affects the distal end portion of the flexible tube 701, the distal end portion of the flexible tube 701 bends in a direction where the incision 710 opens, as shown in FIG. 41.

Therefore, as shown in FIG. 43, at a branched portion of a deep bronchial tube where the endoscope 750 is normally difficult to enter, by bending the distal end portion of the flexible tube 701, the biopsy forceps can be directed to a tube having the tumor 100.

Further, as shown in FIG. 44, by bending the distal end portion of the flexible tube 701 at the incision 100, the tissues can be collected with the forceps cups 702 abutting against the root area of the tumor 100. Thus, accuracy in diagnosing the invasion area of malignant lesion is improved.

It should be noted that the above-described configuration is an example, and various modification may be available. For example, as shown in FIG. 45, the incision may be formed to have a V-shaped cross section, and the operation wire 705 is located on the outside of the flexible tube between a pair of holes 711, which are formed to have the incision 710 therebetween.

With this configuration, by operating the operation wire 705, the distal end portion of the flexible tube 1 can be directed in both sides (as indicated by two-dotted lines) with respect to a neutral position (which is indicated by solid lines).

TWENTY-THIRD EMBODIMENT

FIG. 49 is a cross-sectional side view showing a distal end portion of a high-frequency cutting tool for an endoscope according to an embodiment of the invention.

The high-frequency cutting tool includes an electrically insulating flexible tube 801 which is to be inserted in a treatment tool insertion channel of an endoscope (not shown). The flexible tube 801 is made of tetrafluoroethylene resin, inner/outer diameters of which are approximately 1 mm/2 mm.

Inside the flexible tube 801, a flexible conductive wire 802 formed of twisted stainless-steel wires is inserted over the entire length of the flexible tube 801. The conductive wire 802 is movable along the axis of the flexible tube 801 at an operation unit (not shown). Further, the conductive wire 802 is connected to a high-frequency power supply code at the operation unit, and the high-frequency power is arbitrarily applied.

At a distal end portion of the flexible tube 801 (i.e., at a position 1-5 cm spaced from the distal end of the flexible tube 1), a groove 805, which extends in a direction perpendicular to the axis of the flexible tube 801 and has a V-shaped cross section, is formed. The depth of the groove 805 is set to traverse the inner diameter, and thus, the thickness of the flexible tube 801 remains uncut.

Further, the bottom of the groove 5 is formed to have a curved surface. Therefore, the flexible tube 801 may not be cracked even if it is bent at the groove repeatedly. A pair of holes 803 are formed on the flexible tube 801 with the groove 804 located therebetween. The conductive wire 802 is inserted through the holes 803 so that the conductive wire 802 is located outside the flexible tube 801 at a portion between the two holes 803.

The distal end portion of the flexible tube 801 is tapered (i.e., formed to have a smaller diameter at a distal end side). Inside the tapered portion of the flexible tube 801, a stopper 806, which is fixed on the distal end of the conductive wire 802, is fitted in so that the stopper is fixed to the flexible tube 801.

By pulling the conductive wire 802 at the operation unit, the distal end portion of the flexible tube 801 is bent. Since the portion formed with the groove 805 is much easier to bend than the other portion, bending is achieved mostly at the position where the groove 805 is formed, as shown in FIG. 50.

After the groove 805 is completely closed, the other portion starts to bend. However, in such a case, the force required for pulling the conductive wire 802 increases greatly, and therefore, the operator can recognize the bending condition of the tool.

Thus, if the pulling operation of the conductive wire 802 is stopped when the force necessary for pulling the conductive wire 802 increases remarkably, the distal end portion of the flexible tube 801 is bent at a predetermined bending amount. Therefore, the human tissues can be cut at a desired depth A.

It should be noted that the cutting depth A can be adjusted by distances P and Q (i.e., distances from the groove 805 and the holes 803).

Although twenty-three embodiments are described separately, any suitable combination among the above-described embodiments and variation of the same should also be the subject of the present invention.

The present disclosure relates to the subject matters contained in Japanese Patent Applications No. 2001-050545, filed on Feb. 26, 2001, No. 2001-051580, filed on Feb. 27, 2001, No. 2001-056076, filed on Mar. 1, 2001, No. 2001-056212, filed on Mar. 1, 2001, No. 2001-196466, filed on Jun. 28, 2001, No. 2001-217503, filed on Jul. 18, 2001, and No. 2001-217504, filed on Jul. 18, 2001, and No. 2001-218138, filed on Jul. 18, 2001, which are expressly incorporated herein by reference in their entireties.

What is claimed is:

1. A tubular treatment tool for an endoscope, comprising:

a flexible tubular member, a groove traversing said flexible tubular member in a direction of a diameter of said flexible tubular member;

an operation wire positioned within said flexible tubular member, said operation wire being movable relative to said flexible tubular member along an axis of said flexible tubular member; and a tissue collecting device attached to the distal end of said flexible tubular member, one circumferential portion of a distal end of said operation wire being secured to an inner circumferential surface of the tissue collecting device by brazing and a second circumferential portion of the distal end of said operation wire is not secured to the tissue collecting device, wherein a proximal end portion of the tissue collecting device is provided with protruded portions having a wedge-shaped cross-section that prevents removal of the tissue collecting device from the flexible tubular member, wherein the protruded portions are acuate, and wherein a gap exists between the second circumferential portion of the distal end of said operation wire and the inner circumferential surface of the tissue collecting device.

2. The tubular treatment tool according to claim 1, wherein said groove has a V-shaped cross section.

3. The tubular treatment tool according to claim 1, wherein the tissue collecting device is a spoon tool.

4. The treatment tool according to claim 1, wherein the spoon tool comprises a cutting edge.

5. The treatment tool according to claim 1, wherein the one circumferential portion of the distal end of said operation wire is secured to the inner circumferential surface of the tissue collecting device at a side on which the groove is formed.

* * * * *